(12) United States Patent
Kozmin et al.

(10) Patent No.: US 8,445,481 B2
(45) Date of Patent: May 21, 2013

(54) SCAFFOLD-DIVERSIFIED PYRROLIDINONE DERIVATIVES AND THEIR USE

(75) Inventors: Sergey A. Kozmin, Lake Forest, IL (US); Jiayue Cui, Chicago, IL (US); Robert Haselkorn, Chicago, IL (US); Piotr Gornicki, Chicago, IL (US); Olesya Ulanovskaya, Chicago, IL (US); Stephen Kron, Oak Park, IL (US)

(73) Assignee: The University of Chicago, Chicago, IL (US)

( * ) Notice: Subject to any disclaimer, the term of this patent is extended or adjusted under 35 U.S.C. 154(b) by 264 days.

(21) Appl. No.: 12/543,792

(22) Filed: Aug. 19, 2009

(65) Prior Publication Data

US 2010/0035892 A1 Feb. 11, 2010

Related U.S. Application Data

(63) Continuation-in-part of application No. PCT/US2008/002203, filed on Feb. 20, 2008, and a continuation-in-part of application No. PCT/US2008/002240, filed on Feb. 20, 2008.

(60) Provisional application No. 60/902,594, filed on Feb. 20, 2007.

(51) Int. Cl.
*A61K 31/495* (2006.01)
*A61K 31/437* (2006.01)
*C07D 221/04* (2006.01)
*C07D 209/04* (2006.01)

(52) U.S. Cl.
USPC ............................ 514/215; 514/299; 546/112

(58) Field of Classification Search
None
See application file for complete search history.

(56) References Cited

U.S. PATENT DOCUMENTS

| | | | |
|---|---|---|---|
| 6,903,091 B2 | 6/2005 | Failli et al. | |
| 2003/0149081 A1* | 8/2003 | Zou et al. | 514/343 |
| 2003/0187254 A1 | 10/2003 | Perry et al. | |
| 2004/0009972 A1 | 1/2004 | Ding et al. | |
| 2006/0079499 A1 | 4/2006 | Wu et al. | |
| 2007/0225332 A1 | 9/2007 | Gu et al. | |

OTHER PUBLICATIONS

Nakamura, I. et al. Transition-Metal-Catalyzed Reactions in Heterocyclic Synthesis. Chem. Rev. 2004, vol. 104, p. 2127.*
Chattopadhyay, SK. et al. Formation of medium-ring heterocycles by diene and enyne metathesis. Tetrahedron. 2007, vol. 63, p. 3919.*
Banfi L et al. Ugi Multicomponent Reaction Followed by an Intermolecular Nucleophilic Substitution: Convergent Multicomponent Synthesis of 1-sulfonyl 1,4-diazepan-5-ones and of their benzo-fuzed Derivatives. J. Org. Chem. 2007, vol. 72, p. 2151.*
Corbett, JW. et al. Review of recent acetyl-CoA carboxylase inhibitor patents: mid 2007-2008. Expert Opin. Ther. Patents. 2009, vol. 19(7), p. 943-956.*
Dorwold, FZ. Side Reactions in Organic Synthesis. Wiley. 2005, preface.*
Imming, P., Sinning, C. & Meyer, A. Drugs, their targets and the nature and number of drug targets. Nature Rev. Drug Discov. 5, 821-834 (2006).
Schreiber, S. L. Small molecules: the missing link in the central dogma. Nature Chem. Biol. 1, 64-66 (2005).
Merrifield, R.B. Solid phase peptide synthesis. I. The synthesis of a tetrapeptide. J. Am. Chem. Soc. 85, 2149-2154 (1963).
Matteucci, M.D. & Caruthers, M.H. Studies on nucleotide chemistry IV. Synthesis of deoxyoligonucleotides on a polymer support. J. Am. Chem. Soc. 103, 3185-3191 (1981).
Sears, P. & Wong, C.-H. Toward automated synthesis of oligosaccharides and glycoproteins. Science 291, 2344-2350 (2001).
Gordon, E.M., Barrett, R.W., Dower, W.J., Fodor, S.P.A. & Gallop, M.A. Applications of combinatorial technologies to drug discovery. 2. Combinatorial organic synthesis, library screening strategies, and future directions. J. Med. Chem. 37, 1385-1401 (1994).
Thompson, L.A. & Ellman, J. A. Synthesis and application of small molecule libraries. Chem. Rev. 96, 555-600 (1996).
Burke, M.D. & Schreiber, S.L. A planning strategy for diversity-oriented synthesis. Angew. Chem. Int. Ed. 43, 46-58 (2004).
Guillier, F., Orain, D. & Bradley, M. Linkers and cleavage strategies in solid-phase organic synthesis and combinatorial chemistry. Chem. Rev. 100, 2091-2158 (2000).
Lam, K.S., Lebl, M. & Krchnak, V. The "one-bead-one-compound" combinatorial library method. Chem. Rev. 97, 411-448 (1997).
Ley, S.V. et al. Multi-step organic synthesis using solid-supported reagents and scavengers: a new paradigm in chemical library generation. J. Chem. Soc., Perkin Trans. 1 23, 3815-4195 (2000).
Han, H., Wolfe, M.M., Brenner, S. & Janda, K.D. Liquid-phase combinatorial synthesis. Proc. Natl. Acad. Sci. USA 92, 6419-6423 (1995).
Kim, R.M. et al. Dendrimer-supported combinatorial chemistry. Proc. Natl. Acad. Sci. USA 93, 10012-10017 (1996).
Luo, Z., Zhang, Q., Oderaotoshi, Y. & Curran, D.P. Fluorous mixture synthesis: A fluorous-tagging strategy for the synthesis and separation of mixtures of organic compounds. Science 291, 1766-1769 (2001).

(Continued)

Primary Examiner — Rita Desai
(74) Attorney, Agent, or Firm — Brinks Hofer Gilson & Lione

(57) ABSTRACT

The present disclosure provides novel compounds of the formula (I):

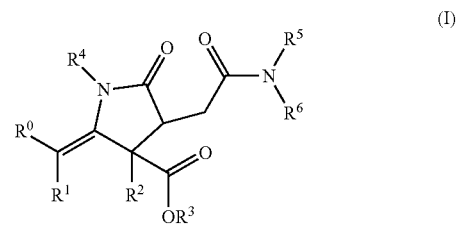

wherein $R^0$, $R^1$, $R^2$, $R^3$, $R^4$, $R^5$, and $R^6$ are as defined in the detailed description. Two preferred compounds of formulae (IX) and (X) are disclosed. Also disclosed are uses of the disclosed compounds, for example, in regulating glucose transport and in inhibiting acetyl coenzyme A carboxylase.

18 Claims, 13 Drawing Sheets

OTHER PUBLICATIONS

Kyranos, J.N., Cai, H., Wei, D. & Goetzinger, W.K. High-throughput high-performance liquid chromatography/mass spectrometry for modern drug discovery. *Curr. Opin. Biotechnol.* 12, 105-111 (2001).

Isbel, J., Xu, R., Cai, Z. & Kassel, D.B. Realities of high-throughput liquid chromatography/mass spectrometry purification of large combinatorial libraries: a report on overall sample throughput using parallel purification. *J. Comb. Chem.* 4, 600-611 (2002).

Matsuo, K. & Tanaka, K. Syntheses of the novel furo[3,4-b][1,5]benzodiazepinone and pyrrol[3,4-b][1,5]benzodiazepinone systems. *Chem. Pharm. Bull.* 32, 3724-3729 (1984).

Bunin, B.A. & Ellman, J.A. A general and expedient method for the solid-phase synthesis of 1,4-benzodiazepine derivatives. *J. Am. Chem. Soc.* 114, 10997-10998 (1992).

DeWitt, S.H., et al. "Diversomers": An approach to nonpeptide, nonoligomeric chemical diversity. *Proc. Natl. Acad. Sci. USA* 90, 6909-6913 (1993).

Beifuss, U. & Ledderhose, S. Annulation reactions with 4-silyloxyquinolinium-salts: a new tool for the highly diastereoselective synthesis of acridines and other condensed N-heterocycles. *Synlett* 1995, 938 (1995).

McGill, J.M., LaBell, E.S. & Williams, M. Hydride reagents for stereoselective reductive amination, an improved preparation of 3-endo-tropanamine. *Tetrahedron Lett.* 37, 3977-3980 (1996).

Cavé, C., Gassama, A., Mahuteau, J., d'Angelo, J. & Riche, C. Condensation of chiral imines and chiral β-enaminoesters with maleic and citraconic anhydrides. *Tetrahedron Lett.* 38, 4773-4776 (1997).

Kanduc, D. et al. Cell death: Apoptosis versus necrosis. *Int. J. Oncology* 21, 165-170 (2002).

Evan, G. & Littlewood, T. A matter of life and cell death. *Science* 281, 1317-1322 (1998).

Hengartner, M.O. The biochemistry of apoptosis. *Nature* 407, 770-776 (2000).

Blatt, N.B. & Glick, G.D. Signaling pathways and effector mechanisms pre-programmed cell death. *Bioorg. Med. Chem.* 99, 1371-1384 (2001).

Huang, Z. The Chemical biology of apoptosis: Exploring protein-protein interactions and the life and death of cells with small molecules. *Chem. Biol.* 9, 1059-1072 (2002).

Kim, R. et al. Current status of the molecular mechanisms of anticancer drug-induced apoptosis. *Cancer. Chemother. Pharmacol.* 50, 343-352 (2002).

Levine, A.J., Finlay, C. A. & Hinds, P.W. P53 is a tumor suppressor gene. *Cell* 116, S67-S70 (2004).

Boitano, A., Ellman, J.A., Glick, G.D. & Opipari, A.W. The proapoptotic benzodiazepine Bz-423 affects the growth and survival of malignant B cells 1. *Cancer Res.* 63, 6870-6876 (2003).

Nesterenko, V., Putt, K.S. & Hergenrother, P.J. Identification from a combinatorial library of a amall molecule that selectively induces apoptosis in cancer cells. *J. Am. Chem. Soc.* 125, 14672-14673 (2003).

Dothager, R.S. et al. Synthesis and identification of small molecules that potently induce apoptosis in melanoma cells through G1 cell cycle arrest. *J. Am. Chem. Soc.* 127, 8686-8696 (2005).

Putt, K.S. et al. Small molecule activation of procaspase-3 to caspase-3 as a personalized anti-cancer strategy. *Nature Chem. Biol.* 2, 543-550 (2006).

Oberhammer, F. et al. Apoptotic death in epithelial cells: cleavage of DNA to 300 and/or 50 kb fragments prior to or in the absence of internucleosomal fragmentation. *EMBO J.* 12, 3679-3684 (1993).

Chan, S. L. et al. Identification of chelerythrine as an inhibitor of BcIXL function. *J. Biol. Chem.* 278, 20453-20456 (2003).

Fadok, V.A. et al. Exposure of phosphatidylserine on the surface of apoptotic lymphocytes triggers specific recognition and removal by macrophages. *J. Immunol.* 148, 2207-2216 (1992).

Koopman, G. et al. Annexin V for flow cytometric detection of phosphatidylserine expression on B cells undergoing apoptosis. *Blood* 84, 1415-1420 (1994).

Darzynkiewicz, Z. et al. Features of apoptotic cells measured by flow cytometry. *Cytometry* 13, 795-808 (1992).

Dive, C. et al. Analysis and discrimination of necrosis and apoptosis (programmed cell death) by multiparameter flow cytometry. *Biochim. Biophys. Acta* 1133, 275-285 (1992).

Vermes, I., Haanen, C. & Reutelingsperger, C. Flow cytometry of apoptotic cell death. *J. Immunol. Methods* 243, 167-190 (2000).

\* cited by examiner

Ketoesters (M)

$M_1$ $M_2$ $M_3$ $M_4$ $M_5$

Amines (R)

955 Single Compounds | Average Yield Per Plate
66%
70%
69%
79%
81%
67%
79%
84%
78%
76%

Representative, Fully Characterized Library Members

1

2

3

4

20
New ACC2 Selective Inhibitor

Structures of other known ACC Inhibitors

Soraphen A    CP-640186

*No reported ACC isotype selectivity*

A-80040 Series

*ACC2 selective*

SCAFFOLD-DIVERSIFIED PYRROLIDINONE DERIVATIVES AND THEIR USE

The present application is a continuation-in-part application of PCT/US2008/002240 and PCT/US2008/002203, both of which were filed on Feb. 20, 2008 and claimed priority to U.S. Provisional Patent Application No. 60/902,594, filed Feb. 20, 2007, the entireties of all of which are hereby incorporated by reference.

FIELD OF THE INVENTION

The present disclosure relates to a method for rapid generation of small-molecule libraries in high chemical purity, compounds discovered by same, and the uses of these compounds.

BACKGROUND OF THE INVENTION

Membrane-permeable small organic molecules comprise the majority of current therapeutic agents. They are also used in the area of chemical biology to perturb and modulate the function of biomolecules in vitro and in vivo. Identification of new bioactive compounds often relies on screening of large collections of compounds, known as chemical libraries. Unlike the solid-phase synthesis of peptides, oligonucleotides and oligosaccharides, all of which have greatly advanced over the years, high-throughput synthesis of small-molecule libraries in high chemical purity remains to be a challenge. Several methods of generation of chemical libraries have been developed over the years. However, each of these methods suffers from several problems, which preclude their wide-spread applications in academics and pharmaceutical industry.

Solid-phase synthesis enables facile generation of molecular diversity, particularly via the split-and-pool method. For small-molecule libraries, however, this strategy suffers from the laborious process of reaction optimization and frequently results in moderate purities of the final compounds, once detached from the solid support. Low chemical purity results in large numbers of false positive hits in biological assays.

Solution-phase synthesis using soluble oligomeric or polymeric support requires derivatization and cleavage of each individual compound from such support. Significant amount of time is generally required for optimization of reaction conditions. While the solution-based approaches enable more rapid reaction optimization and higher chemical purities, these advances come at the expense of significantly higher costs, which arise from the use of polymer-supported reagents, the development of appropriate soluble polymeric supports, or the expensive instrumentation required for robotic chromatographic purification of the final compounds.

Another approach relies on parallel synthesis and robotically-driven automated HPLC purification of each individual compound. While reaction optimization is efficient and final products with high purity are produced, this strategy requires highly specialized equipment, and requires significant investment of resources and supplies.

It is thus desirable to develop a practical and general strategy for rapid and efficient generation of new small-molecule libraries in high chemical purity.

BRIEF SUMMARY OF THE INVENTION

The present disclosure provides novel compounds of the formula (I):

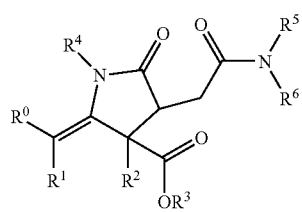

wherein $R^0$, $R^1$, $R^2$, $R^3$, $R^4$, $R^5$, and $R^6$ are as defined below. Two preferred compounds of formulae (IX) and (X) are disclosed.

At another aspect, a method of assaying the activity of an enzyme is disclosed by contacting a target molecule with the enzyme in the presence of any of the compounds disclosed above; and evaluating the activity of the enzyme.

In yet another aspect, a method of inhibiting acetyl coenzyme A carboxylase (ACC) comprises administering a therapeutically effective amount of any compound as disclosed in the present disclosure, or a pharmaceutically acceptable salt thereof, such that the activity of ACC is at least partially inhibited.

In still another aspect, a method for treating a human that has a disease state that is alleviated by treatment with an ACC inhibitor is disclosed. The method comprises administering a therapeutically effective amount of any compound as disclosed in the present disclosure, or a pharmaceutically acceptable salt thereof, to a human in need thereof.

In yet still another aspect, a method for treating a human that has cancer is disclosed. The method comprises administering a therapeutically effective amount of any compound as disclosed in the present disclosure, or a pharmaceutically acceptable salt thereof, to a human in need thereof.

In further another aspect, a composition comprises any compound as disclosed in the present disclosure, or a pharmaceutically acceptable salt thereof.

In further still another aspect, a pharmaceutical composition comprises any compound as disclosed in the present disclosure, or a pharmaceutically acceptable salt thereof, and a pharmaceutical acceptable carrier.

DETAILED DESCRIPTION OF THE DISCLOSURE

Figure 1A:
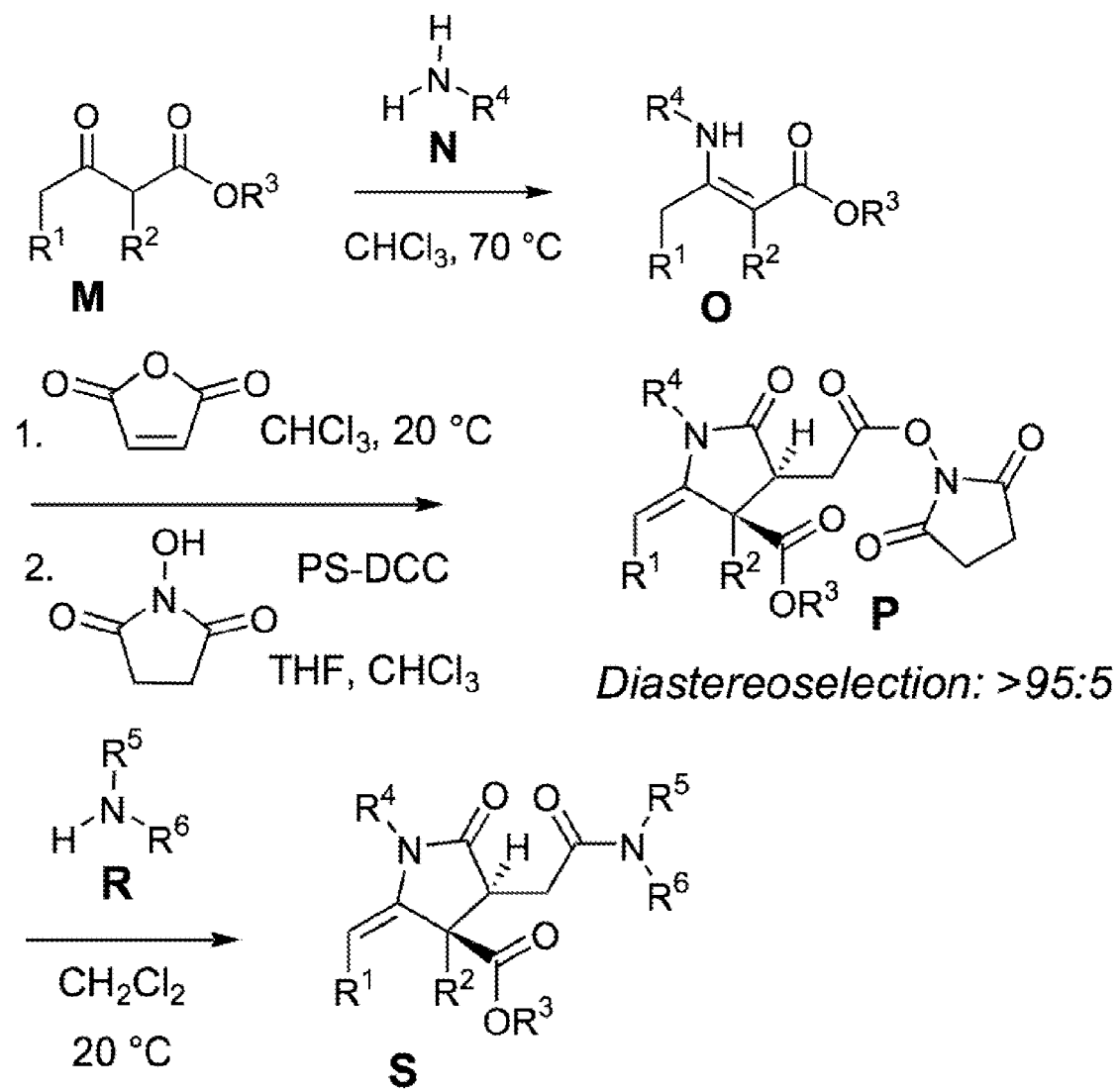
FIG. 1 illustrates the synthesis of scaffold-diversified pyrrolidinone library. (a) Four-step synthetic sequence, which was employed for library production. (b) Structures of ketoesters $M_1$-$M_5$, which were employed for the synthesis of corresponding vinylogous amides O. (c) Structures of amines $N_1$-$N_{16}$, which were used for the synthesis of corresponding vinylogous amides O. (d) Structures of amines $R_1$-$R_{12}$, which were used for the final amidation and library production in a 96-well format on 2.5 μmol scale. (e) Purity analysis of the entire library by analytical TLC and determination of average chemical yields per each 96-well plate by 500 MHz $^1$H NMR analysis of 12 randomly selected compounds per plate. (f) Structures of 5 representative library members, which were randomly selected and fully characterized by $^1$H NMR, $^{13}$C NMR and MS.

The present disclosure is directed to a broadly useful, practical strategy, which would enable rapid and efficient parallel synthesis and purification of a wide range of new chemical libraries. This strategy allows preparation of a sufficient amount of material for the broad high-throughput screening of each compound in a large number of cell-based and target-based assays. This strategy also allows development of an economical and practical protocol, which would enable efficient high-throughput synthesis and rapid parallel purification of each final compound. This method also provides access to a sufficient amount of material for accurate determination of the efficiency of each reaction and characterization of the purity of each final compound by NMR spectroscopy. The present disclosure is also directed to compounds discovered by this strategy.

Definitions

When describing the compounds, compositions, methods and processes of this disclosure, the following terms have the following meanings, unless otherwise indicated.

The term "hydroxy" means the —OH group.

The term "halogen" or "halo" means a chlorine, bromine, iodine, or fluorine atom.

The term "alkyl" means a hydrocarbon group that may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "cycloalkyl" means an alkyl group that is cyclic.

The term "alkenyl" means a hydrocarbon group that contains at least one carbon-to-carbon double bond. The term "alkynyl" means a hydrocarbon group that contains at least one carbon-to-carbon triple bond. Alkenyl and alkynyl groups can be substituted or unsubstituted, unless otherwise indicated.

The term "aryl" means a polyunsaturated, aromatic hydrocarbon group having 5-10 atoms and forming a single ring (monocyclic, preferably with 6 atoms such as phenyl) or multiple rings (bicyclic (preferably with 10 atoms such as naphthyl) or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "deprotecting agent" refers to any suitable compound or combination of compounds which capable of removing a specified protecting group and restores the unprotected functional group.

The term "heteroaryl" means an aromatic group containing 5-10 atoms and at least one heteroatom (such as S, N, O, Si), where the heteroaryl group may be monocyclic (with preferably 5 or 6 atoms) or bicyclic (with preferably 9 or 10 atoms). Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "heterocyclyl" or "heterocyclic", which are synonymous as used herein, means a saturated or unsaturated non-aromatic ring containing at least 5-10 atoms (preferably 5 or 6) and at least one heteroatom (typically 1 to 5 heteroatoms) selected from nitrogen, oxygen or sulfur. The heterocyclyl ring may be monocyclic (with preferably 5 or 6 atoms) or bicyclic (with preferably 9 or 10 atoms). Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "carbocyclic" means a ring composed exclusively of carbon atoms.

The term "substituent" means an atom or a group that replaces another atom or group in a molecule.

The term "alkoxy" refers to —O-alkyl. Examples of an alkoxy group include methoxy, ethoxy, n-propoxy, etc.

The term "haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

All of the above terms (e.g., "alkyl," "aryl," "heteroaryl" etc.), in some embodiments, include both substituted and unsubstituted forms of the indicated groups. These groups may be substituted multiple times, as chemically allowed.

Certain compounds of the present disclosure can exist in unsolvated forms as well as solvated forms, including hydrated forms. In general, both solvated forms and unsolvated forms are intended to be encompassed within the scope of the present disclosure. Certain compounds of the present disclosure may exist in multiple crystalline or amorphous forms (i.e., as polymorphs). In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present disclosure, whether radioactive or not, are intended to be encompassed within the scope of the present disclosure.

Compounds

In one embodiment, the compound of the present disclosure is of the formula (I):

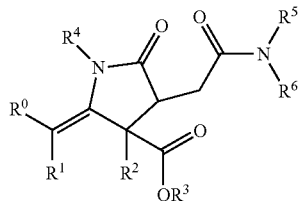

(I)

where $R^0$, $R^1$, and $R^2$ are each independently hydrogen, halogen, substituted or unsubstituted $C_{1-20}$ alkyl, substituted or unsubstituted $C_{2-8}$ alkenyl, substituted or unsubstituted $C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R'", —NR'R", —NR'CO$_2$R", —NR'S(O)$_2$R", —SR', —S(O)R', —S(O)$_2$R', —S(O)$_2$NR'R", substituted or unsubstituted $C_{6-10}$ aryl, substituted or unsubstituted 5- to 10-membered heteroaryl, substituted or unsubstituted 3- to 10-membered heterocyclyl, or an azide functionalized group thereof, where $R^3$ is hydrogen, halogen, substituted or unsubstituted $C_{1-20}$ alkyl, substituted or unsubstituted $C_{2-8}$ alkenyl, substituted or unsubstituted $C_{2-8}$ alkynyl, —CN, —NO$_2$, —C(O)R', —CO$_2$R', —C(O)NR'R", —NR'C(O)R', —NR'C(O)NR"R'", —NR'R", —NR'CO$_2$R", —NR'S(O)$_2$R", substituted or unsubstituted $C_{6-10}$ aryl, substituted or unsubstituted 5- to 10-membered heteroaryl, substituted or unsubstituted 3- to 10-membered heterocyclyl, or an azide functionalized group thereof, where $R^4$, $R^5$, and $R^6$ are each independently hydrogen, halogen, substituted or unsubstituted $C_{1-20}$ alkyl, substituted or unsubstituted $C_{2-8}$ alkenyl, substituted or unsubstituted $C_{2-8}$ alkynyl, —CN, —NO$_2$, —C(O)R', —CO$_2$R', —C(O)NR'R", substituted or unsubstituted $C_{6-10}$ aryl, substituted or unsubstituted 5- to 10-membered heteroaryl, substituted or unsubstituted 3- to 10-membered heterocyclyl, or an azide functionalized group thereof, where $R^1$ and $R^2$ or $R^5$ and $R^6$ may, together with the atoms to which they are attached, form a substituted or unsubstituted 3- to 10-membered ring, and where R', R" and R'" are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl; and R' and R" or R" and R'" may, together with the atoms to which they are attached, form a substituted or unsubstituted 3- to 10-membered ring.

In one embodiment (Ia), $R^0$ in the formula I is hydrogen. In another embodiment (Ib), in formulae I or Ia, $R^1$ and $R^2$, together with the atoms to which they are attached, form a substituted or unsubstituted 5- to 10-membered ring which is carbocyclic, aryl, heterocyclic, or heteroaryl. In another embodiment (Ic), in formulae (I, Ia or Ib), $R^3$ is hydrogen or substituted or unsubstituted $C_{1-20}$ alkyl; preferably $R^3$ is ethyl. In another embodiment (Id), in formulae (I, Ia, Ib or Ic), $R^5$ and $R^6$, together with the atoms to which they are attached, form a substituted or unsubstituted 5- to 10-membered ring which is carbocyclic, aryl, heterocyclic, or heteroaryl.

In another embodiment, the compound of the present disclosure is of the formula (II):

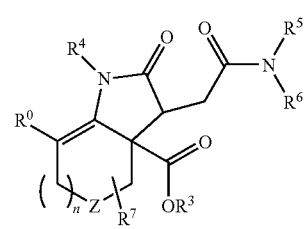

(II)

where Z is carbon, nitrogen, oxygen, or sulfur,
where n is 0-3, and
where $R^7$ can substitute any open valence of any ring within structure, and $R^7$ is hydrogen, halogen, substituted or unsubstituted $C_{1-20}$ alkyl, substituted or unsubstituted $C_{2-8}$ alkenyl, substituted or unsubstituted $C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R'", —NR'R", —NR'CO$_2$R", —NR'S(O)$_2$R", —SR', —S(O)R', —S(O)$_2$R', —S(O)$_2$NR'R", substituted or unsubstituted $C_{6-10}$ aryl, substituted or unsubstituted 5- to 10-membered heteroaryl, substituted or unsubstituted 3- to 10-membered heterocyclyl, or an azide functionalized group thereof.

$R^0$, $R^3$, $R^4$, $R^5$, and $R^6$ are as described above for formula (I-Id). Preferably, n is 2, Z is carbon, and $R^0$ and $R^7$ are hydrogen.

In yet another embodiment, the compound of the present disclosure is of the formula (III):

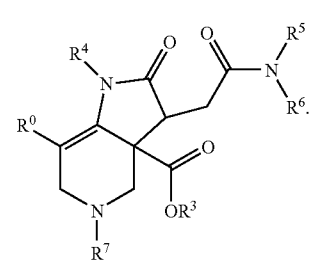

(III)

where $R^0$, $R^3$, $R^4$, $R^5$, $R^6$, and $R^7$ are as described above for formula (II).

In still another embodiment, the compound of the present disclosure is of the formula (IV):

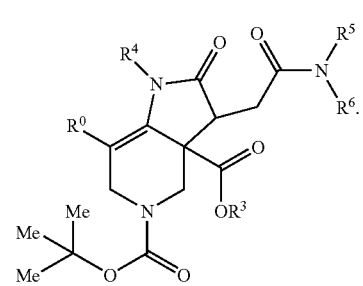

(IV)

where $R^0$, $R^3$, $R^4$, $R^5$, and $R^6$ are as described above for formula (I-Id).

In another embodiment, the compound of the present disclosure is of the formula (V):

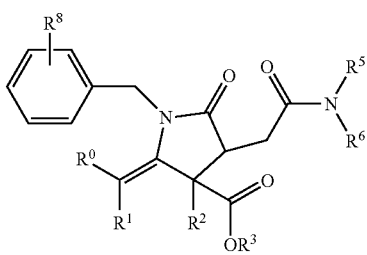

(V)

where R⁸ can substitute any open valence of any ring within structure, and R⁸ is hydrogen, halogen, substituted or unsubstituted $C_{1-20}$ alkyl, substituted or unsubstituted $C_{2-8}$ alkenyl, substituted or unsubstituted $C_{2-8}$ alkynyl, —CN, —NO$_2$, —C(O)R', —CO$_2$R', —C(O)NR'R'', —OR', —OC(O)R', —OC(O)NR'R'', —NR'C(O)R'', —NR'C(O)NR''R''', —NR'R'', —NR'CO$_2$R'', —NR'S(O)$_2$R'', —SR', —S(O)R', —S(O)$_2$R', —S(O)$_2$NR'R'', substituted or unsubstituted $C_{6-10}$ aryl, substituted or unsubstituted 5- to 10-membered heteroaryl, substituted or unsubstituted 3- to 10-membered heterocyclyl, or an azide functionalized group thereof, or two R⁸ groups may, together with the atoms to which they are attached, form a substituted or unsubstituted 3- to 10-membered ring.

R⁰, R¹, R², R³, R⁵, and R⁶ are as described above for formula (I-Id). In one example, R⁸ is halogen.

In still another embodiment, the compound of the present disclosure is of the formula (VI):

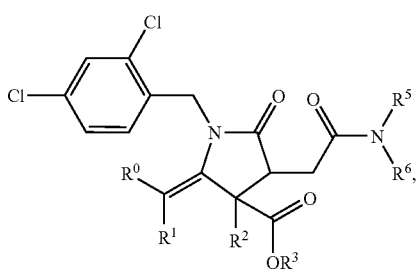

(VI)

where R⁰, R¹, R², R³, R⁵, and R⁶ are as described above for formula (I-Id).

In yet another embodiment, the compound of the present disclosure is of the formula (VII):

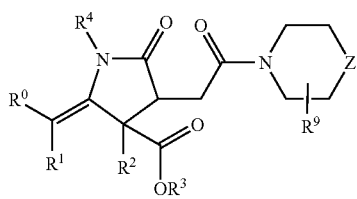

(VII)

where Z is carbon, nitrogen, oxygen, or sulfur, and
where R⁹ can substitute any open valence of any ring within structure, and R⁹ is hydrogen, halogen, substituted or unsubstituted $C_{1-20}$ alkyl, substituted or unsubstituted $C_{2-8}$ alkenyl, substituted or unsubstituted $C_{2-8}$ alkynyl, —CN, —NO$_2$, —C(O)R', —CO$_2$R', —C(O)NR'R'', —OR', —OC(O)R', —OC(O)NR'R'', —NR'C(O)R'', —NR'C(O)NR''R''', —NR'R'', —NR'CO$_2$R'', —NR'S(O)$_2$R'', —SR', —S(O)R', —S(O)$_2$R', —S(O)$_2$NR'R'', substituted or unsubstituted $C_{6-10}$ aryl, substituted or unsubstituted 5- to 10-membered heteroaryl, substituted or unsubstituted 3- to 10-membered heterocyclyl, or an azide functionalized group thereof, or two R⁹ groups may, together with the atoms to which they are attached, form a substituted or unsubstituted 3- to 10-membered ring.

R⁰, R¹, R², R³, and R⁴ are as described above for formula (I-Id).

In further another embodiment, the compound of the present disclosure is of the formula (VIII):

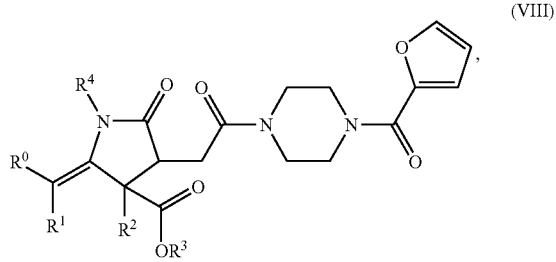

(VIII)

where R⁰, R¹, R², R³, and R⁴ are as described above for formula (I-Id).

In yet another embodiment, the compound of the present disclosure is of the formula (IX):

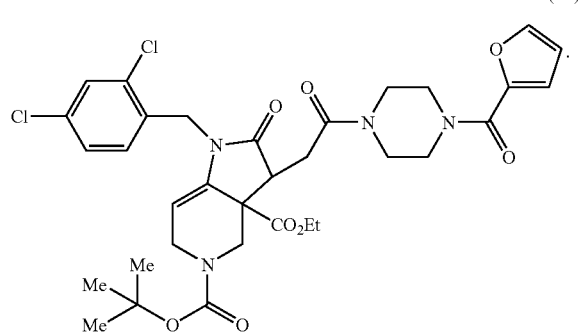

(IX)

In still another embodiment, the compound of the present disclosure is of the formula (X):

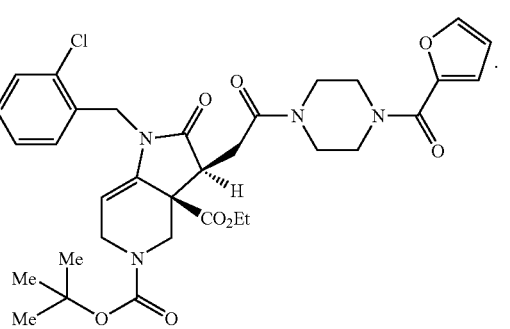

(X)

In another aspect, a method of assaying the activity of an enzyme is disclosed. The method comprises contacting a target molecule with the enzyme in the presence of any of the compounds disclosed above; and evaluating the activity of the enzyme.

In one example, the enzyme is acetyl coenzyme A carboxylase (ACC). In another example, the compound selectively inhibits one isotype of an acetyl coenzyme A carboxylase.

In yet another aspect, a method of inhibiting ACC comprises administering a therapeutically effective amount of any compound as disclosed above, or a pharmaceutically acceptable salt thereof, such that the activity of ACC is at least partially inhibited.

Human and animal ACC exists as two isoenzymes, ACC1 and ACC2. In one example, the activity of ACC1 is at least partially inhibited. In another example, the activity of ACC2 is at least partially inhibited. Preferably, any compound as disclosed above, or a pharmaceutically acceptable salt thereof, selectively inhibits the activity of ACC2. More preferably, the activity of ACC1 is substantially not inhibited by any compound as disclosed above, or a pharmaceutically acceptable salt thereof.

In another embodiment, there is provided a method of treating cancer in a subject comprising administering to a cancer cell in a subject any of the compounds disclosed above.

As used herein, "treating" or "treatment" of a cancer, tumor or neoplastic condition in subject includes one or more of: (1) inhibiting a tumor, i.e., arresting its development, (2) inhibiting or reducing growth of a tumor in a subject, i.e., arresting or preventing metastases, (3) enhancing the antiproliferative effect of chemotherapy and/or gene therapy in a subject, i.e., improving the subject's response to a treatment regime. The present methods will be of use in the clinical treatment of neoplastic cells, abnormal growth of cells and/or hyperproliferative cells, various types of cancer and/or tumors. As used herein, the term "neoplastic" means an abnormal growth of a cell or tissue (e.g., a tumor) which may be benign or cancerous. As used herein, "abnormal growth of cells" and/or "hyperproliferative cells" are meant to refer to cell growth independent of normal regulatory mechanisms (e.g., loss of contact inhibition), including the abnormal growth of benign and malignant cells or other neoplastic diseases. As used herein, the term "tumor" includes neoplasms that are identifiable through clinical screening or diagnostic procedures including, but not limited to, palpation, biopsy, cell proliferation index, endoscopy, mammography, digital mammography, ultrasonography, computed tomography (CT), magnetic resonance imaging (MRI), positron emission tomography (PET), radiography, radionuclide evaluation, CT- or MRI guided aspiration cytology, and imaging-guided needle biopsy, among others. Such diagnostic techniques are well known to those skilled in the art and are described in Holland, et al., *Cancer Medicine,* 4th Ed., Vol. One, Williams & Wilkins, Baltimore, Md. (1997).

"Inhibiting a neoplastic cell," as used herein, refers to inducing apoptosis, anoikis or necrosis, and/or interfering with cell division, disrupting normal functionality of microtubules, inhibiting utilization of a metabolite, substituting nucleotide analogs into cellular DNA, or inhibiting enzymes necessary for DNA replication, in the cell to which the construct and chemotherapeutic agent is delivered. Inhibiting may comprise inhibiting cancer cell growth, inhibiting cancer cell proliferation, inhibiting cancer cell survival, inhibiting cancer cell invasion, inhibiting cancer cell migration, restoring growth control of said cancer cell, or inducing cancer cell death. The neoplastic cell may be a cancer cell, for example, a lung cancer cell, prostate cancer cell, ovarian cancer cell, testicular cancer cell, brain cancer cell, skin cancer cell, colon cancer cell, rectal cancer cell, gastric cancer cell, esophageal cancer cell, tracheal cancer cell, head & neck cancer cell, pancreatic cancer cell, liver cancer cell, breast cancer cell, ovarian cancer cell, lymphoid cancer cell, leukemia cell, cervical cancer cell, or vulvar cancer cell. Such treatment may also be particularly useful tools in the treatment of neoplastic diseases and/or cancers, for example, in treating patients with lung cancer, prostate cancer, ovarian cancer, testicular cancer, brain cancer, skin cancer, colon cancer, rectal cancer, gastric cancer, esophageal cancer, tracheal cancer, head & neck cancer, pancreatic cancer, liver cancer, breast cancer, ovarian cancer, lymphoid cancer, leukemia, cervical cancer, vulvar cancer or melanoma.

For example, the cancer may be breast, prostate, ovarian, brain, melanoma, colorectal, liver, lymphoma, lung, oral, head, neck, spleen, lymph node, small intestine, large intestine, blood cells, stomach, pancreatic, endometrium, testicle, skin, esophagus, bone marrow, blood, cervical, bladder, Ewing's sarcoma, thyroid, a glioma, and/or gastrointestinal. The invention is applicable to other cancers discussed herein, including pre-cancers.

Examples of solid tumors that can be treated with the compositions and methods described herein include, but are not limited to carcinomas, sarcomas, blastomas or gliomas. In certain aspects solid tumors include epidermoid tumors, squamous tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal carcinomas and sarcomas, rhabdomyosarcoma, glioblastoma, preferably glioblastoma multiforme, and leiomyosarcoma. Examples of vascularized skin cancers that can be treated include squamous cell carcinoma, basal cell carcinoma and skin cancers such as human malignant keratinocytes. In certain aspects, other solid tumors include, but are not limited to, endothelial cell carcinoma. Examples of endothelial cell carcinoma include, but are not limited to, renal cell carcinoma (clear cell carcinoma, papillary carcinoma, chromophobe carcinoma, collecting duct carcinoma and unclassified carcinoma), colon carcinoma, transitional cell carcinoma, lung carcinoma (adenocarcinoma, alveolar cell carcinoma, squamous cell carcinoma, large cell and small cell carcinoma), breast carcinoma and prostatic adenocarcinoma can also be treated with compositions and methods of the invention.

The method may further comprise administering to said cell a second anti-cancer therapy, such as a chemotherapeutic agent, a radiotherapeutic, a hormone therapy, an immunotherapy, or surgery.

The term "chemotherapeutic agent" refers to a therapeutic compound and/or drug which may be used to, among other things, treat cancer. For example, a chemotherapeutic agent may include, but is not limited to, any agent that interferes with cell division, disrupts normal functionality of microtubules, inhibits utilization of a metabolite, substitutes nucleotide analogs into cellular DNA, or inhibits enzymes necessary for DNA replication.

Ionizing radiation means radiation comprising particles or photons that have sufficient energy or can produce sufficient energy via nuclear interactions to introduce ionization (gain or loss of electrons). An exemplary and preferred ionizing radiation is an x-radiation. Means for delivering x-radiation to a target tissue or cell are well known in the art. Electromagnetic radiation includes, but is not limited to, x-rays and gamma rays. Particulate radiation includes, but is not limited to, electron beams, proton beans, neutron beams, alpha particles, and negative pimesons.

Methods may further comprise any of the compounds administered together with an antiproliferative drug, e.g. a chemotherapeutic drug, e.g. as used in cancer treatment, including but not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide, or with an anti-diabetic drug, an insulin secretagogue or insulin secretion enhancer, e.g. a sulphonyl urea, e.g. tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcyclamide, an oral insulinotropic agent derivative, e.g. a short acting insulin enhancer, e.g. meglitinide, repaglinide, a phenyl acetic acid derivative, e.g. nateglinide, a DPP IV inhibitor, e.g. 1-{2-[(5-cyanopyridin-2-yl)amino]ethylamino}acetyl-(2S)-cyano-pyrrolidine dihydrochloride, LAF237, GLP-1 or a GLP-1 agonist analog, or an insulin sensitizer e.g. a peroxisome proliferator activated receptor γ agonist (PPARy), e.g. a glitazone, a non-glitazone type such as a N-(2-benzoylphenyl)-L-tyrosine analogue, e.g. GI-262570, or an oxolidinedione, e.g. JTT501, a dual PPAR.gamma./PPAR.alpha. agonist, e.g. DRF-554158, NC-2100 or NN-622, a retinoid X receptor agonist or a rexinoid, e.g. 2-[1-(3,5,5,8,8-pentamethyl-5,6,7,8-tetrahydro-2-naphthyl)-cyclopropyl]-pyridine-5-carboxylic acid, 4-[(3,5, 5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof.

In still another aspect, a method for treating a human that has a disease state that is alleviated by treatment with an ACC inhibitor is disclosed. The method comprises administering a therapeutically effective amount of any compound as disclosed above, or a pharmaceutically acceptable salt thereof, to a human in need thereof. The disease state may be metabolic syndrome, type II diabetes, or obesity.

In further another aspect, a composition comprises any compound as disclosed above, or a pharmaceutically acceptable salt thereof.

In further still another aspect, a pharmaceutical composition comprises any compound as disclosed above or a pharmaceutically acceptable salt thereof, and a pharmaceutical acceptable carrier.

Assembly of Scaffold-Diversified Pyrrolidinone Library

Referring to Scheme 1, reaction of vinylogous amides O with cyclic unsaturated anhydrides, i.e. maleic anhydride, enables the assembly of pyrrolidinones via the initial Michael addition, followed by intramolecular amide formation and tautomerization into enamides P. This tandem reaction sequence can be carried out under mild conditions (typically at 20° C.), representing an attractive synthetic entry into a new small-molecule library. Indeed, a condensation of 5 ketoesters M with 18 amines N is expected to produce 80 vinylogous amides O. Subsequent construction of pyrrolidinone core by simple treatment with maleic anhydride, followed by activation of the carboxylic acid sets the stage for the final diversification, which would entail condensations with 12 additional amines producing a chemical library of 960 amides S. The use of cyclic ketoesters M would enable diversification of the molecular scaffold by variation of the connectivity between $R^1$ and $R^2$ groups (vide infra). The increase in skeletal diversity of small-molecule libraries is attractive since it results in the assembly of structurally more dissimilar chemotypes, increasing the probability of new lead identification in broad-based high-throughput screening.

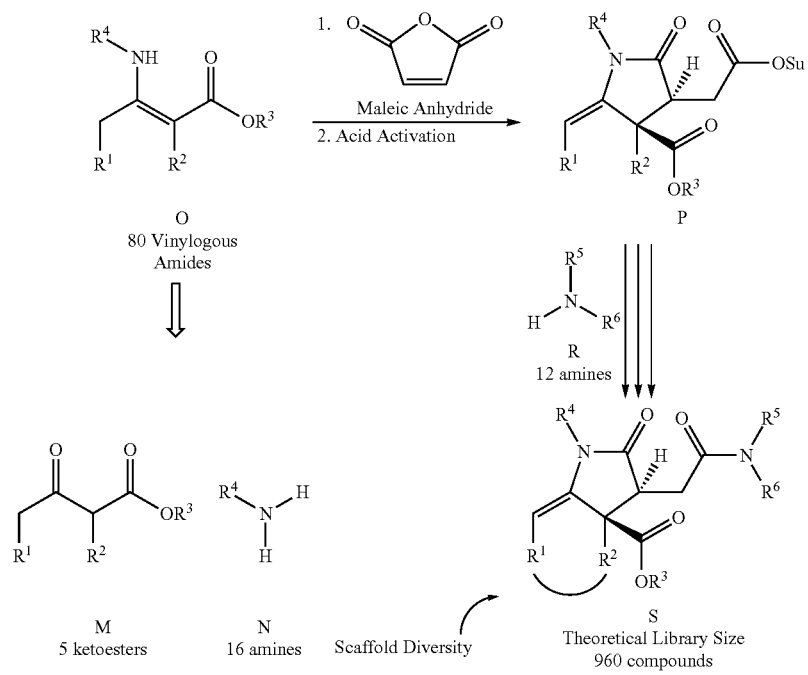

Scheme 1 Design of the scaffold-diversified pyrrolidinone library.

Figure 1B:
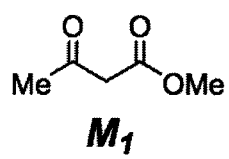
Figure 1B:
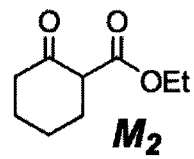
Figure 1B:
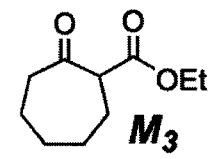
Figure 1B:
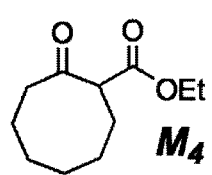
Figure 1B:
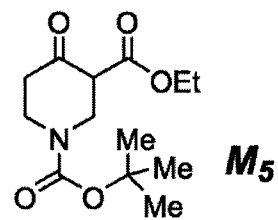
Figure 1C:
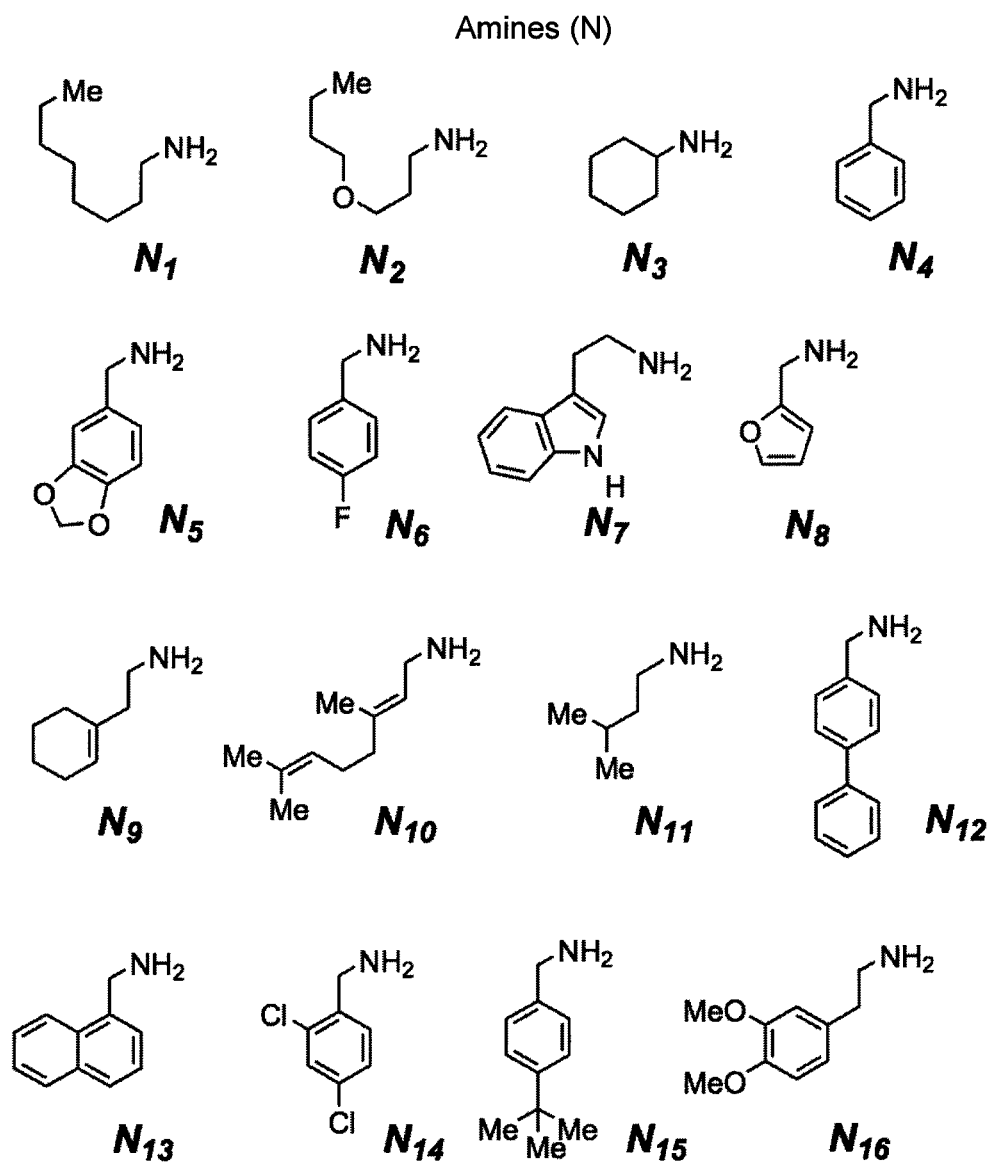
Figure 1D:
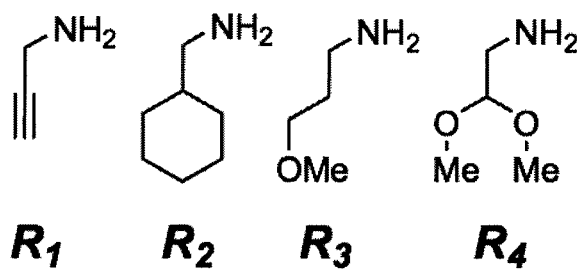
Figure 1D:
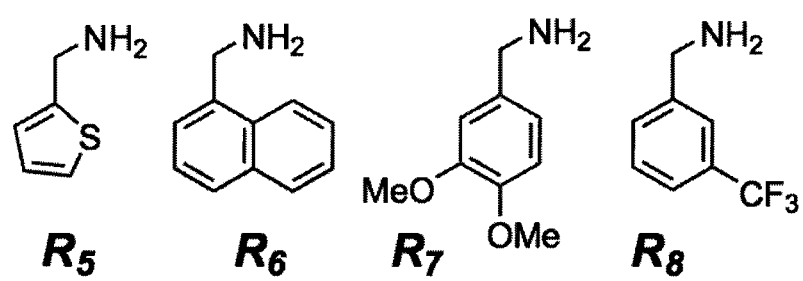
Figure 1D:
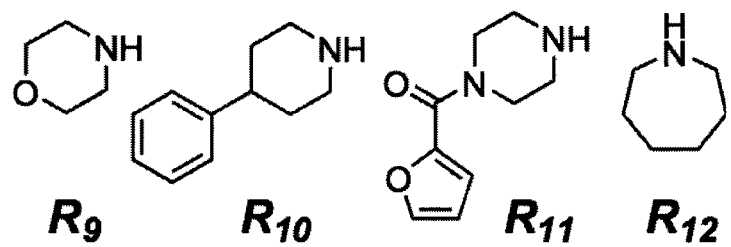
Figure 1E:
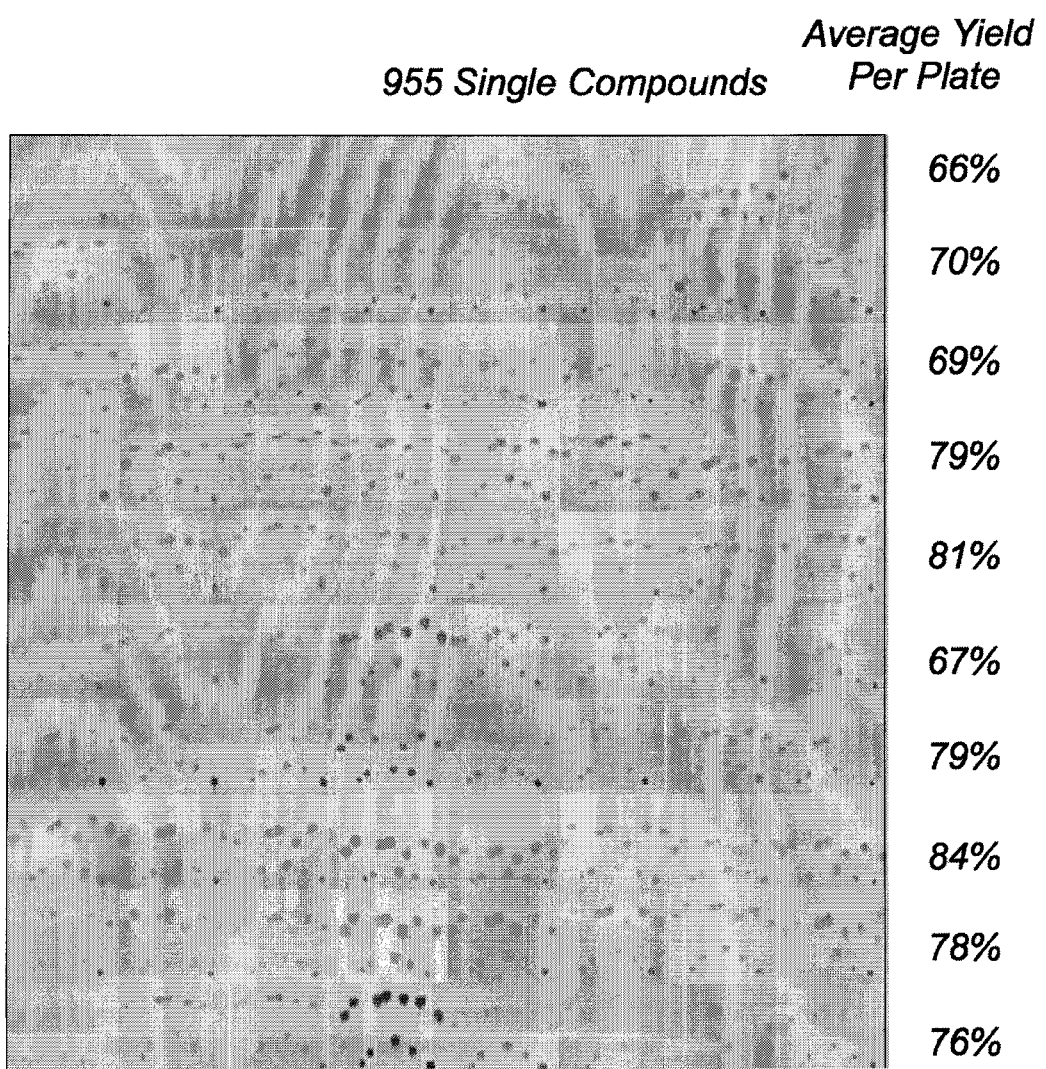
Figure 1F:
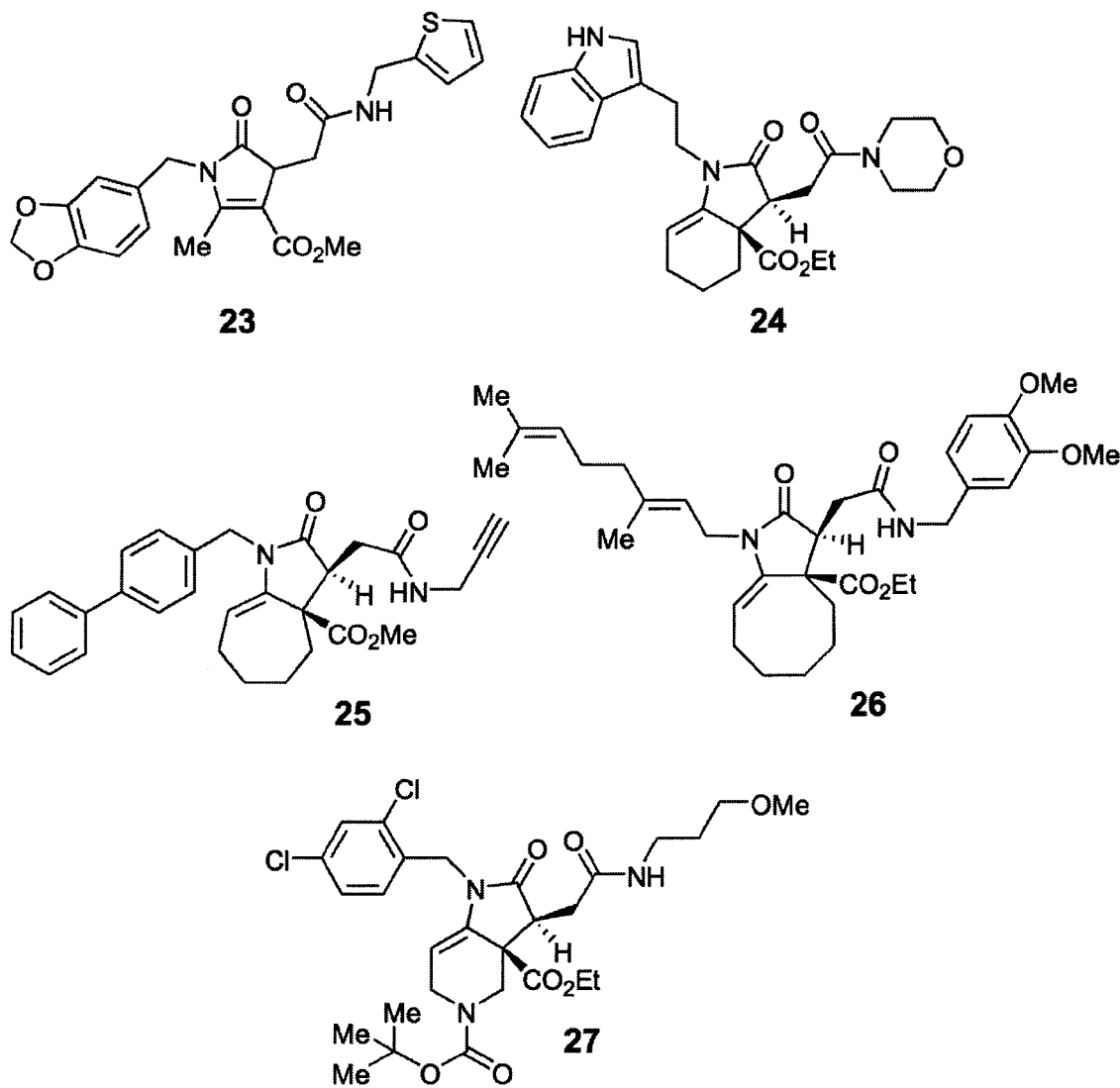

Referring to FIG. 1, construction of the chemical library began with condensation of ketoesters M with primary amines N, which occurred at about 70° C. in $CHCl_3$ and afforded the desired vinylogous amides O, typically in about 60-90% yield after silica gel purification. Upon examination of a variety of possible building blocks, 5 ketoesters $M_{1-5}$ and 16 primary amines $N_{1-16}$ were selected for the first stage of the library production. Construction of pyrrolidinones was performed by treatment of vinylogous amides O with maleic anhydride in $CHCl_3$ at about 20° C., followed by conversion of the resulting carboxylic acids into the corresponding N-hydroxy-succinimide esters P using resin-bound carbodiimide to facilitate chromatographic purification of activated esters. The final stage of the library production entailed condensation of amines $R_{1-12}$ with N-hydroxy-succinimide esters P, which was carried on a 2.5 mol scale in a 96-well format, followed by parallel purification of each individual library member. Analysis of purity and efficiency by TLC of all compounds and $^1H$ NMR of 120 randomly selected compounds revealed that 955 compounds were produced successfully in average purity of greater than about 90% and average chemical yields per plates ranging from about 66% to about 84%. Several representative library members 23-27 were fully characterized to establish their identity. Their structures are representative of the level of skeletal diversity, which was achieved by the design of our synthetic strategy.

Identification of Small-Molecule Inhibitors of Acetyl Coenzyme A Carboxylases

ACCs are key metabolic enzymes, which catalyze the formation of malonyl-coenzyme A by ATP-dependent carboxylation of acetyl-coenzyme A, which is believed to be the rate-determining step for fatty acid biosynthesis. Inhibition of human ACCs is believed to be a promising treatment of obesity and diseases related to the disorder of fatty acid metabolism, such as type II diabetes, dyslipidemia, metabolic syndrome and cancer. Human and animal ACC exists as two isoenzymes, ACC1 and ACC2. ACC1 is a 265 KDa protein that locates in the cytosol, while ACC2 (280 KDa) bears an additional 114 amino acid residues at the N-terminus, and locates itself in the mitochondrial membrane. Inhibition of ACC1 leads to decreased fatty acid synthesis, while the inhibition of ACC2 up-regulates the fatty acid consumption in mitochondria. Both of them result in the reduction of fatty acid level in the cell. Recent studies have shown that ACC2 gene knock-out mice are healthy and fertile, showing decreased body weight despite increased food intake. However, the ACC1 gene knock-out mice are embryonically lethal. Therefore selective inhibitors of ACC2 represent promising drug leads in the metabolic diseases therapeutic area.

The incidence of type 2 diabetes has dramatically increased over the past decade. This epidemic is largely attributed to proliferation of key risk factors, which include a sedentary lifestyle, a high fat diet, obesity and the demographic shift to a more aged population. There is ample evidence to indicate that increased abdominal obesity and physical inactivity contribute significantly to the development of type 2 diabetes.

At the cellular level, an increase in ectopic fat storage in nonadipose tissues such as in muscle, liver and pancreas is a strong predictor of the development of insulin resistance and type 2 diabetes. The precise mechanism of how increased intracellular lipid content exacerbates whole body insulin sensitivity is unclear at present but it has been postulated that increased long chain fatty acyl-CoAs, ceramide or diacylglycerol, whose contents are proportional to the accumulation of intramyocellular triglyceride, antagonizes metabolic actions of insulin, reduces muscle glucose uptake and inhibits hepatic glucose production. As muscle is the primary site of metabolic action of insulin, the development of muscle insulin resistance along with liver insulin resistance are thus inherently linked to the development of whole body insulin resistance.

In order to increase muscle and liver fat oxidation and thus limit the concentration of long chain fatty acyl CoAs, the activity of ACC was inhibited, which catalyzes the production of malonyl-CoA from acetyl-CoA. Malonyl-CoA is an intermediate substrate that plays an important role in the overall fatty acid metabolism: Malonyl-CoA is utilized by fatty acid synthase for de novo lipogenesis, and also acts as a potent allosteric inhibitor of carnitine palmitoyltransferase 1 (CPT1), a mitochondrial membrane protein that shuttles long chain fatty acyl CoAs into the mitochondrial where they are oxidized. A small molecule inhibitor, of ACC would thus limit de novo lipid synthesis, de-inhibit CPT1 and subsequently increase fat oxidation.

In rodents and in humans, there are two known isoforms of ACC that are encoded by distinct genes and share approximately 70% amino acids identity. ACC1, which encodes a 265 KD protein, is highly expressed in the cytosol of lipogenic tissues such as liver and adipose, whereas 280 KD ACC2 protein is preferentially expressed in oxidative tissues, skeletal muscle and heart. ACC2 has a unique 114 amino acid N-terminus with a putative transmembrane domain (TM), which is thought to be responsible for mitochondrial targeting. Based on tissue distribution and subcellular localization of these two isoforms, the current hypothesis is that a distinct pool of Malonyl-CoA produced by ACC1 is preferentially converted into fatty acids by fatty acid synthase, whereas another pool of Malonyl-CoA synthesized primarily by ACC2, presumed localized in near mitochondria, is involved in the inhibition of CPT1. Therefore, ACC1 inhibition reduces fatty acid synthesis and is beneficial for use in treating diseases such as metabolic syndrome.

Genetic studies have demonstrated that ACC2 knockout mice are healthy and fertile with a favorable metabolic phenotype, increased fatty acid oxidation, increased thermogenesis, reduced hepatic TG content and subsequent decrease in body weight despite increase in food intake compared to their littermates. In addition, these mice are resistant against high fat diet-induced obesity and insulin resistance. Also, recently it was demonstrated that the effects of leptin and adiponectin, cytokines secreted from adipose tissue, to increase fatty acid oxidation are at least due in part to the inhibition of ACC in liver and skeletal muscle. Taken together these data support that the discovery of small molecular inhibitors of ACC2 can provide a favorable metabolic profile against obesity induced type 2 diabetic patients. Further-more, the dual inhibition of ACC1 and ACC2 can provide the profile needed to demonstrate benefit for patients exhibiting conditions of metabolic syndrome.

Compounds and compositions of the present disclosure are useful for inhibiting the effects of ACC, and more particularly that of ACC2 selectively. In particular, the compounds and compositions of the present disclosure may be used for treating and preventing disorders modulated by ACC. Such disorders may be ameliorated by selectively inhibiting the ACC in a mammal, preferably by administering a compound or composition of the present disclosure, either alone or in combination with another active agent, for example, as part of a therapeutic regimen.

The compounds of the present disclosure, including but not limited to those specified in the examples, inhibit ACC. As inhibitors of ACC, the compounds of the present disclosure can be useful for the treatment and prevention of a number of ACC mediated diseases or conditions.

Compounds of the present disclosure may be useful for the treatment or prevention of metabolic syndrome, type II diabetes, obesity, atherosclerosis and cardiovascular diseases in humans.

Dysregulation of fatty acids metabolism contributes to decreased insulin sensitivity and the development of metabolic syndrome. ACC is known to modulate fatty acid synthesis and fatty acid oxidation in insulin responsive tissues such as liver, adipose and skeletal muscles. The ACC inhibitors of the present disclosure, have the potential to decrease de novo lipid synthesis and increase fat oxidation in vivo. Therefore, these chemotypes represent a novel method to treat insulin resistance/type 2 diabetes, as well as obesity, hypertension and hyperlipidemia.

Figure 2A:
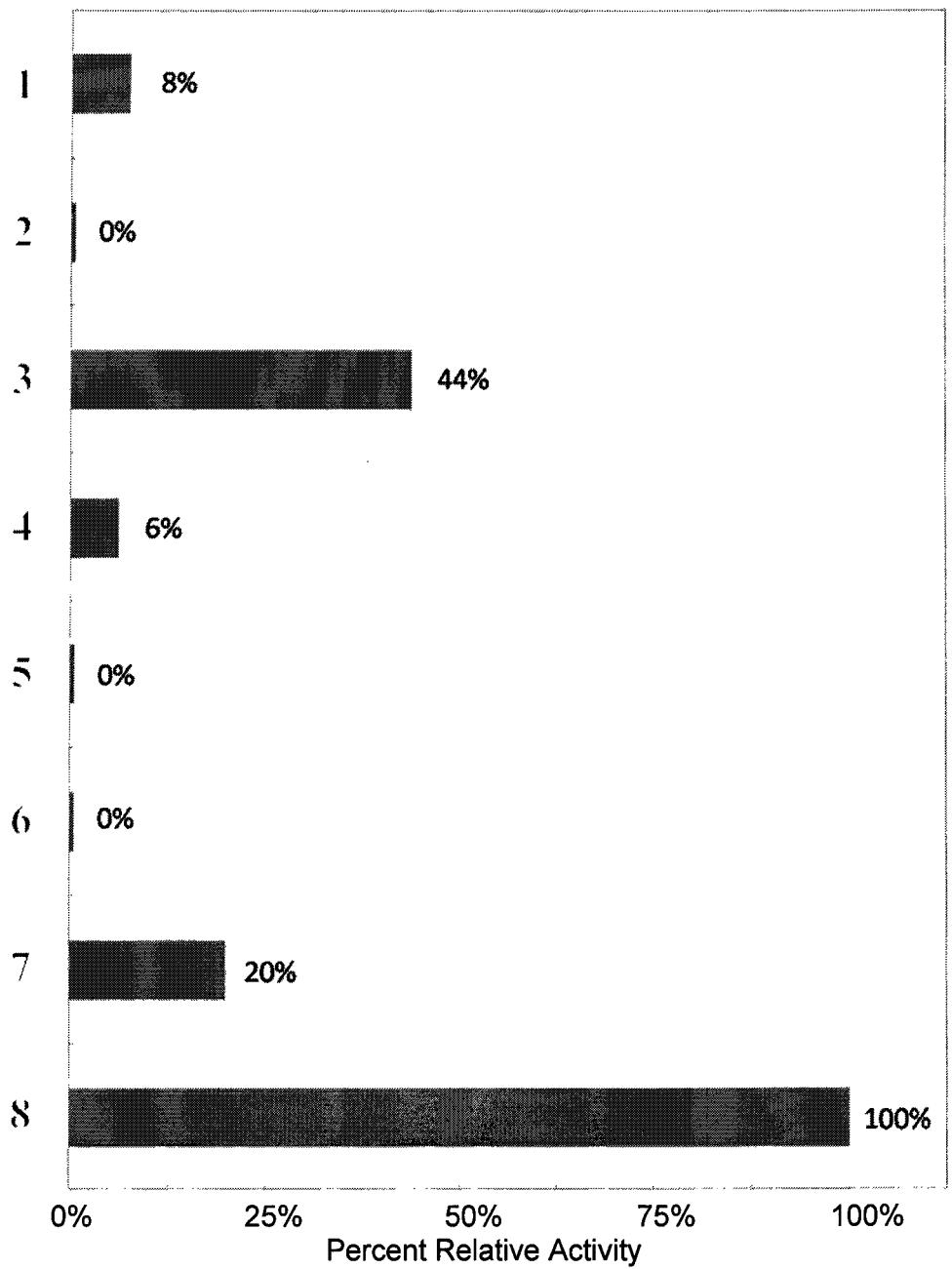
FIG. 2 illustrates the percent relative activity of ACC2-selective inhibitor 20 and other members from the pyrrolidinone library.
Figure 2B:
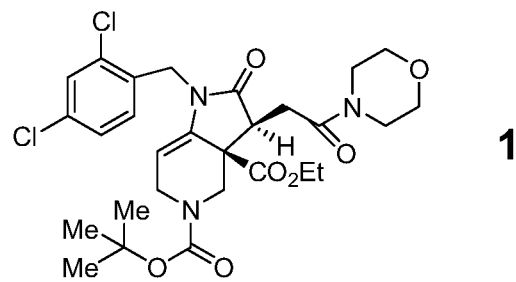
Figure 2B:
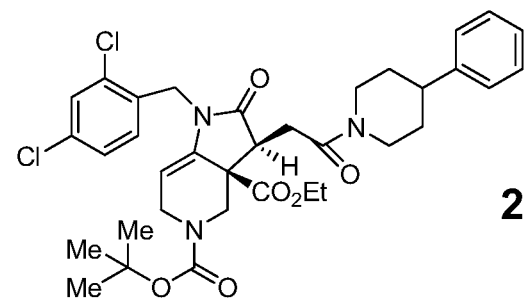
Figure 2B:
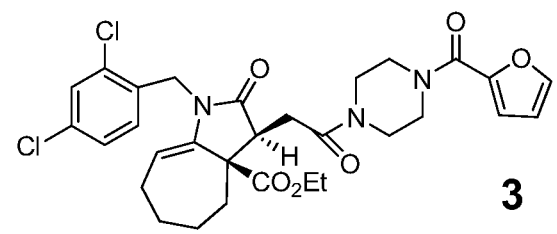
Figure 2B:
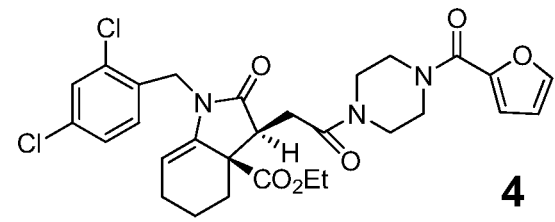
Figure 2C:
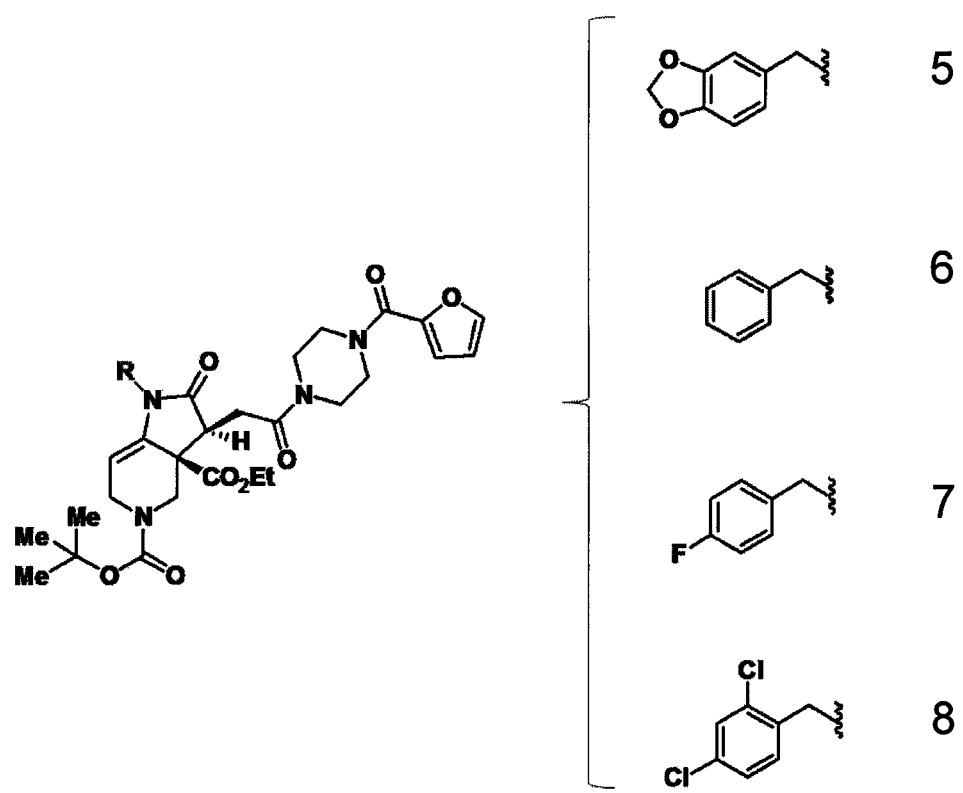
Figure 3A:
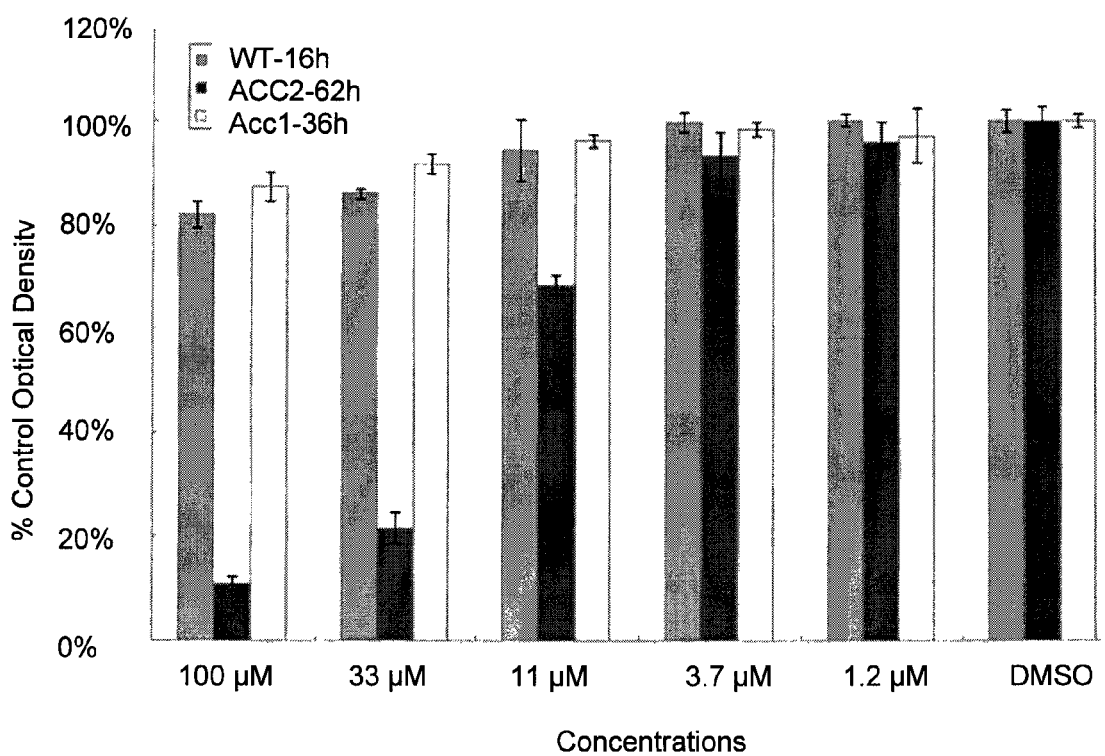
FIG. 3 illustrates a new acetyl coenzyme A carboxylase (ACC) isotype-selective inhibitor. (a) The bar graph illustrates that ACC2-selective inhibitor 20 preferentially inhibited the growth of hACC2 overexpressed Saccharomyces Cerevisiae yeast cells in a dose-dependent manner, while possessing minimum toxicity against wild type and hACC1 overexpressed cells. (b) Structure of ACC2-selective inhibitor 20. (c) Structures and isotype-selectivity of other ACC inhibitors. The assay was performed by screening the library in wild type, hACC1 overexpressed and hACC2 overexpressed yeast cells.
Figure 3B:
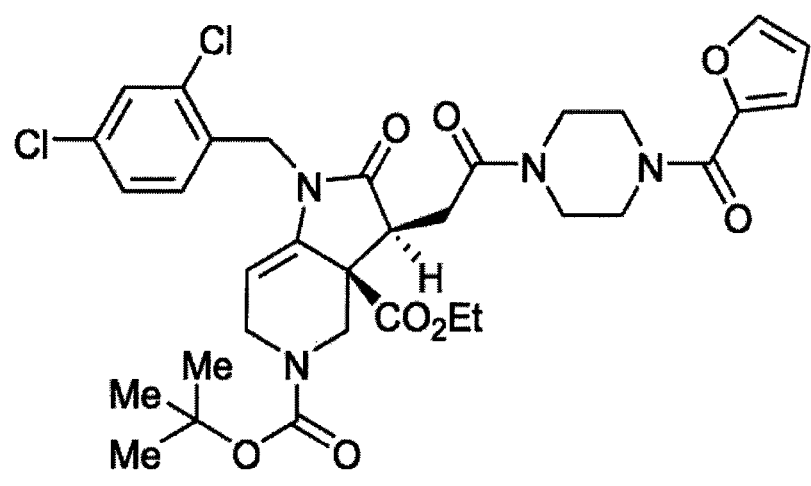
Figure 3C:
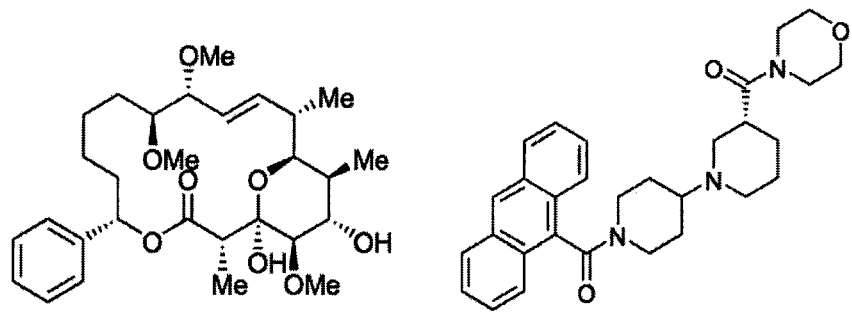
Figure 3C:
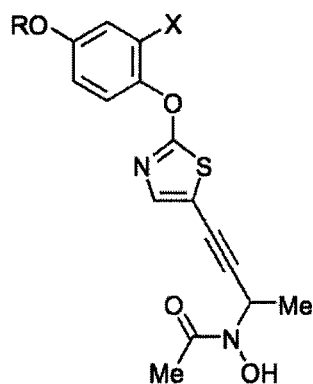
Figure 4A:
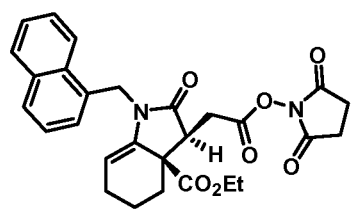
FIG. 4 illustrates the chemical structure and crystal structure of succinimide ester A7B4-HOSu.
Figure 4B:
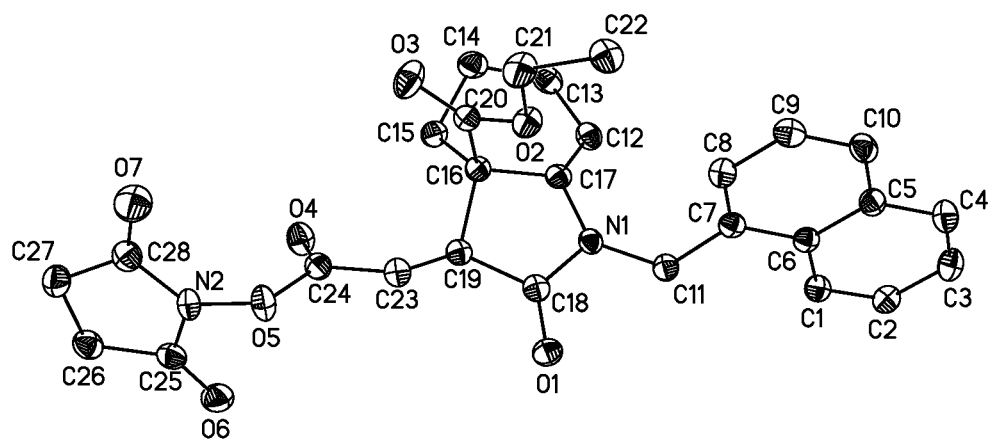

Referring to FIGS. 2 and 3, the ability of the pyrrolidinone library to inhibit enzymatic activity of acetyl coenzyme A carboxylases (ACCs) was evaluated using an ACC activity assay. The ACC activity assay enables rapid and accurate measurement of activity of each of the human ACC isotypes by engineering *Saccharomyces Cerevisiae* strains overexpressing hACC1 and hACC2. Growth of the corresponding yeast strains is dependent on the activity of the two enzymes.

Still referring to FIGS. 2 and 3, high-throughput screen of the pyrrolidinone library enabled the discovery of a new ACC inhibitor 20. After the initial screen, the activity of 20 was validated following re-synthesis on a larger scale and dose-dependent activity evaluation. This compound is able to inhibit ACC2 in an isotype-selective manner and with low overall toxicity, as shown from the dose-dependence data sets. A-80040, another ACC inhibitor, was shown to possess certain level of ACC2 specificity. The structures of 20 and A-80040, however, exhibit little, if any, structural homology, suggesting a different mode of interaction of the two compounds with the protein target.

Development of Small Molecules that Inhibit Glycolysis

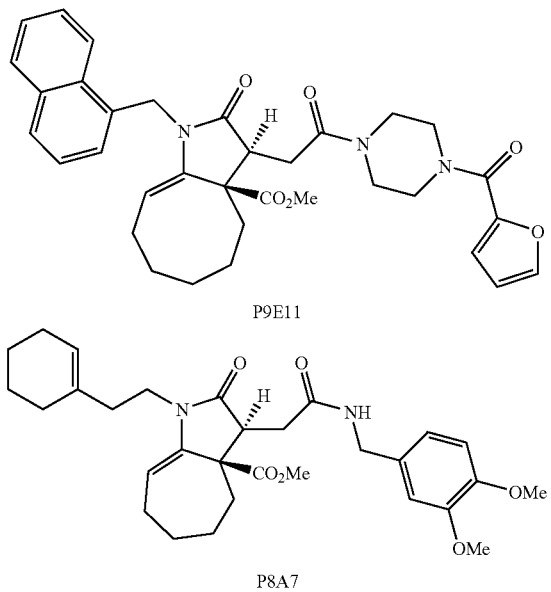

P9E11

P8A7

The pyrrolidinone library was also screened for discovery of new glycolytic inhibitors. Glycolysis is a series of metabolic processes by which glucose is converted to pyruvate, releasing energy in a form of ATP. Subsequently, pyruvate is reduced to the waste product lactic acid. Glycolytic metabolism is very inefficient, producing only two molecules of ATP per one molecule of glucose. Most mammalian cells generate energy via glycolysis only under oxygen-limited conditions. In the presence of oxygen, pyruvate can be further metabolized to carbon dioxide and water, generating additional 36 molecules of ATP. This process is called cellular respiration, and it is the main ATP generation pathway in mammalian cells. In 1924, Otto Warburg noted that tumor cells generate their energy via glycolysis rather than respiration even when sufficient oxygen is available. This phenomenon is called the "Warburg effect", and it constitutes the physiological basis for [$^{18}$F]fluorodeoxyglucose positron emission tomography (FDG-PET). FDG-PET is now widely used as a tumor diagnostic method and was proven to be an effective detection technique. Due to the increased dependency of tumor cells on glycolysis, and its likely role in promoting cell proliferation, survival and invasion, disruption of glycolytic energy metabolism in cancer cells is of interest for the development of a new class of anticancer agents.

EXAMPLES

Methods And Materials. Dichloromethane (HPLC grade), ethyl acetate (ACS grade), hexanes (ACS grade), diethyl ether (ACS grade) were purchased from Fisher Scientific and used without further purification. Anhydrous tetrahydrofuran was purified by distillation from sodium-benzophenone. Commercially available reagents were used without further purification. Reactions were monitored by thin layer chromatography (TLC) using Whatman precoated glass silica gel plates. Flash column chromatography was performed over Silacycle silica gel (230-400 mesh). $^1$H NMR and $^{13}$C NMR spectra were recorded on Bruker DRX-400 or DMX-500 spectrometers using residual solvent peaks as an internal standard. Mass Spectra were recorded with a VG Instruments Model 7070EQ tandem mass spectrometer. All cell lines, media, serum and supplements were purchased from ATCC. CellTiter-Glo® luminescent cell viability assay was purchased from Promega. SensoLyte™ Homogeneous AMC Caspase-3/7 Assay Kit was purchased from AnaSpec. Propidium Iodide, Vybrant® apoptosis assay kit #2 (Alexa Fluor 488 annexin V/propidium iodide) and Hoechst 33342 were purchased from Invitrogen. Culture dishes, 96-well plates and all other supplies were purchased from Fisher Scientific. Luminescence was measured on Perkin-Elmer Victor 3 plate reader.

Pyrrolidinone Library Synthesis. The following procedure represents the synthesis of the first set of 96 compounds, which is designated as plate 1. Eight 1.5 mL polypropylene Eppendorf centrifuge tubes were charged with CHCl$_3$ (about 0.8 mL per tube) and methyl acetoacetate M$_1$ (about 0.5 mmol, about 54 µl per tube). The resulting solutions were treated with amines N$_1$-N$_8$ (about 0.5 mmol) and heated to about 70° C. in a sand bath. Upon completion, the resulting vinylogous amides O$_1$-O$_8$ were purified by preparative TLC (elution with ethyl acetate:hexanes=about 1:5 to 1:1), dissolved in CHCl$_3$ (about 0.8 mL) and treated with maleic anhydride (about 0.3-0.5 mmol, about 29-49 mg per tube) at about 20° C. Upon completion, the reaction mixtures were diluted with CHCl$_3$ (about 0.8 mL) and THF (about 2.4 mL), followed by treatment with N-hydroxysuccinimide (about 0.38-0.63 mmol, about 43-66 mg per tube) and PS-carbodiimide resin (about 1.1 mmol/g, about 345-573 mg per tube). The reaction mixtures were stirred for 2-4 h at about 20° C., filtered, concentrated and purified by preparative TLC (elution with ethyl acetate:hexanes=about 2:1) to give the corresponding eight succinimide esters $P_1$-$P_8$, which were diluted with $CH_2Cl_2$ to final concentrations of about 0.1 M. The about 25 μl portions of each resulting stock solutions were transferred into a polypropylene 96-well PCR plate, and treated with 12 amines $R_1$-$R_{12}$ (about 4 μmol per well) and $CH_2Cl_2$ (about 30 μl per well). After about 30 min at about 20° C., the reaction mixtures were transferred onto preparative TLC plates as described above for the benzodiazepine library. The plates were developed using ethyl acetate:hexanes=about 3:2. The products were detected using UV light and removed from TLC plates as circular silica gel pallets using a metal hole-punching tool (Fisher). The final compounds were removed from silica gel as described above for the benzodiazepine library as initial silica gel pallets, followed by elution with about 0.6 mL of ethyl acetate. Analysis of purity and chemical yields was performed by TLC and NMR as described above for the benzodiazepine library. The resulting 96 compounds were dissolved in DMSO to produce about 10 mM stock solutions, which were stored at about −80° C.

This protocol was used to prepare plate 2 (from ketoester $M_2$, amines $N_1$-$N_8$, and amines $R_1$-$R_{12}$), plate 3 (from ketoester $M_3$, amines $N_1$-$N_8$, and amines $R_1$-$R_{12}$), plate 4 (from ketoester $M_4$, amines $N_1$-$N_8$, and amines $R_1$-$R_{12}$), plate 5 (from ketoester $M_5$, amines $N_1$-$N_8$, and amines $R_1$-$R_{12}$), plate 6 (from ketoester $M_1$, amines $N_9$-$N_{16}$, and amines $R_1$-$R_{12}$), plate 7 (from ketoester $M_2$, amines $N_9$-$N_{16}$, and amines $R_1$-$R_{12}$), plate 8 (from ketoester $M_3$, amines $N_9$-$N_{16}$, and amines $R_1$-$R_{12}$), plate 9 (from ketoester $M_4$, amines $N_9$-$N_{16}$, and amines $R_1$-$R_{12}$), and plate 10 (from ketoester $M_5$, amines $N_9$-$N_{16}$, and amines $R_1$-$R_{12}$).

General Protocols. General Protocol G: Preparation of Vinylogous Amides

Example 1

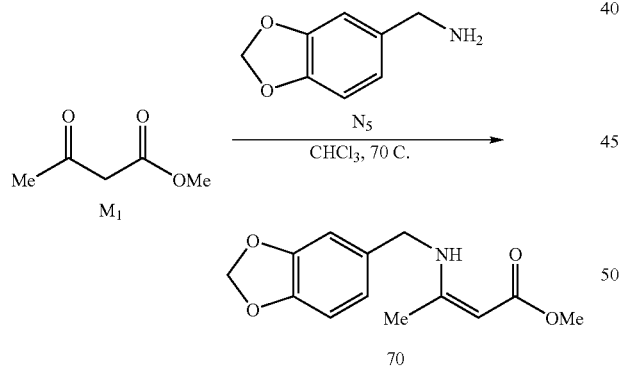

Ketoester $M_1$ (23.2 mg 0.2 mmol) was dissolved in 0.8 ml of $CHCl_3$ in a 1.5 ml polypropylene Eppendorf centrifuge tube, and treated with amine $N_5$ (45.3 mg, 37.4 μl, 0.3 mmol). The tube was capped and heated to 70° C. using a sand bath. The progress of the reaction was monitored by TLC. Upon completion, the reaction mixture was concentrated under reduced pressure and purified by flash chromatography on silica gel (ethyl acetate:hexanes=1:5 to 1:1) to give 44.8 mg (90%) of vinylogous amide 70. $^1$H NMR (400 MHz, $CDCl_3$) δ 8.85 (br s, 1H), 6.69-6.77 (m, 3H), 4.93 (s, 2H), 4.52 (s, 1H), 4.31 (d, 2H, J=6.4 Hz), 3.62 (s, 3H), 1.91 (s, 3H); $^{13}$C NMR (125 MHz, $CDCl_3$), δ 170.82, 161.71, 148.03, 146.85, 132.48, 119.91, 108.36, 107.36, 101.03, 82.76, 49.94, 46.58, 19.31; MS (APCI) calculated for $C_{13}H_{15}NO_4$ 249.10 ($M^+$), found 250.1 (M+H)

Example 2

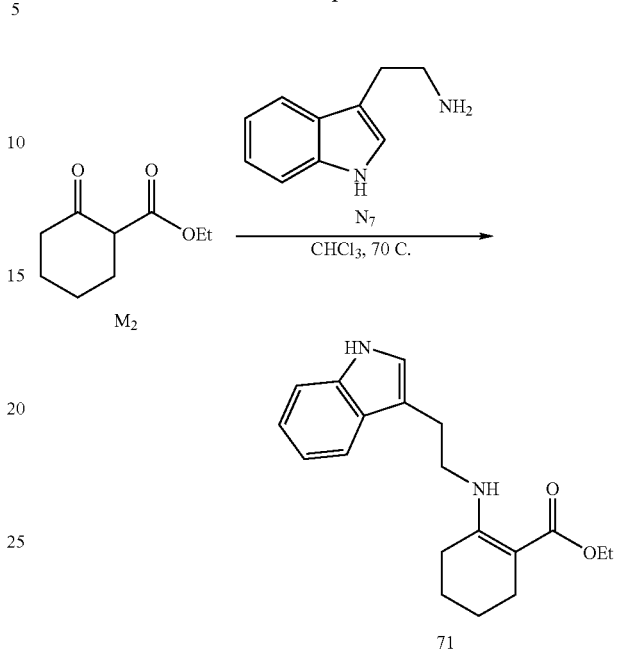

The title compound was prepared in 84% yield according to General Protocol G. $^1$H NMR (500 MHz, $CDCl_3$) δ 9.07 (br s, 1H), 8.16 (br s, 1H), 7.58 (d, 1H, J=7.5 Hz), 7.33 (d, 1H, J=8 Hz), 7.20 (t, 1H, J=7 Hz), 7.13 (t, 1H, J=7.5 Hz), 7.04 (d, 1H, J=2.5 Hz), 4.14 (q, 2H, J=7.2 Hz), 3.49 (dt, 2H, J=7 Hz, 6 Hz), 3.02 (t, 2H, J=7.3 Hz), 2.28-2.30 (m, 4H), 1.61-1.63 (m, 2H), 1.54-1.57 (m, 2H), 1.28 (t, 3H, J=7 Hz); $^{13}$C NMR (125 MHz, $CDCl_3$) δ 170.88, 159.51, 136.26, 127.15, 122.21, 121.91, 119.22, 118.50, 112.89, 111.20, 89.36, 58.58, 42.81, 26.52, 26.43, 23.80, 22.66, 22.25, 14.65.

Example 3

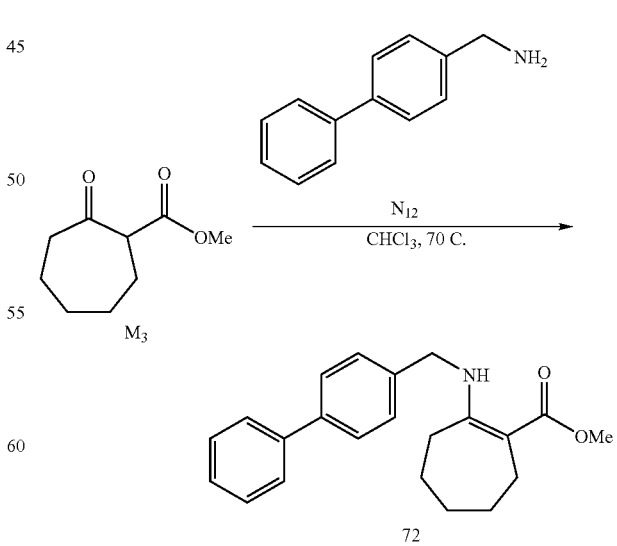

The title compound was prepared in 79% yield according to General Protocol G. $^1$H NMR (500 MHz, $CDCl_3$) δ 9.72 (br s, 1H), 7.57-7.60 (m, 4H), 7.43-7.46 (m, 2H), 7.34-7.36 (m, 3H), 4.50 (d, 2H, J=6.5 Hz), 3.69 (s, 3H), 2.48-2.53 (m, 4H), 1.68-1.70 (m, 2H), 1.45-1.50 (m, 4H); $^{13}$C NMR (125 MHz, CDCl$_3$) δ 171.00, 167.45, 140.71, 140.04, 138.69, 128.72, 127.34, 127.21, 127.17, 126.99, 95.07, 50.40, 46.58, 31.78, 28.74, 28.34, 25.86, 25.02.

Example 4

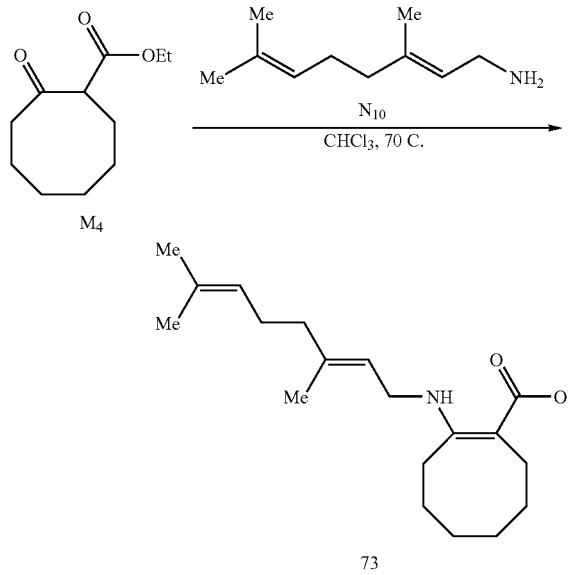

The title compound was prepared in 57% yield according to General Protocol G. $^1$H NMR (400 MHz, CDCl$_3$) δ 9.15 (br s, 1H), 5.24-5.26 (m, 1H), 5.07-5.09 (m, 1H), 4.10 (q, 2H, J=7.1 Hz), 3.79-3.82 (m, 2H), 2.48-2.51 (m, 2H), 2.40 (br, 2H), 2.05-2.10 (m, 2H), 1.98-2.01 (m, 2H), 1.59-1.67 (m, 11H), 1.45-1.50 (m, 6H), 1.24 (t, J=7 Hz). $^{13}$C NMR (100 MHz, CDCl$_3$) δ 170.70, 163.20, 138.33, 131.66, 123.88, 121.55, 91.74, 58.42, 40.88, 39.46, 30.62, 28.58, 26.71, 26.34, 26.25, 25.66, 25.51, 17.68, 16.30, 14.70.

Example 5

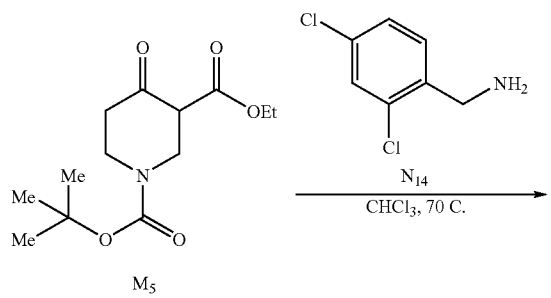

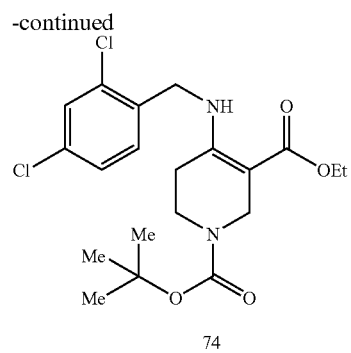

The title compound was prepared in 73% yield according to General Protocol G. $^1$H NMR (500 MHz, CD$_3$CN, 298 K) δ 9.15 (s, 1H), 7.48 (d, 1H, J=2 Hz), 7.27-7.37 (m, 2H), 4.45 (d, 2H, J=6.5 Hz), 4.10 (q, 2H, J=7 Hz), 4.00 (s, 2H), 3.41 (t, 2H, J=6 Hz), 2.33 (t, 2H, J=6 Hz), 1.43 (s, 9H), 1.22 (t, 3H, J=7.3 Hz). $^{13}$C NMR (125 MHz, CD$_3$CN, 298 K) δ 169.49, 158.77, 155.25, 137.18, 134.25, 134.19, 130.73, 130.07, 128.54, 80.07, 59.82, 44.00, 28.52, 26.26, 14.85.

General Protocol H: Preparation of Activated Esters

Example 6

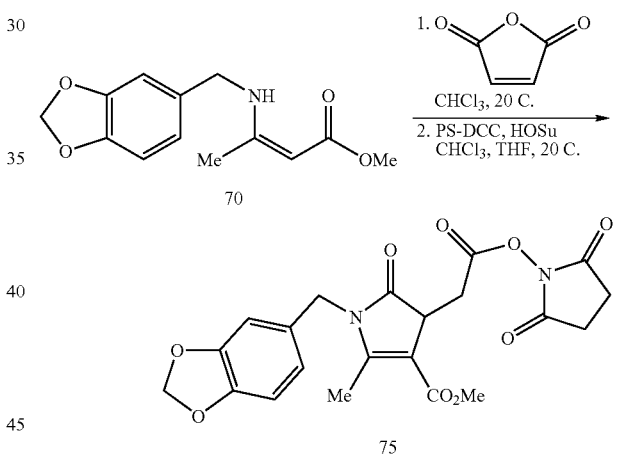

Vinylogous amide 70 (43.1 mg, 0.173 mmol) was dissolved in CHCl$_3$ (0.8 ml) and treated with maleic anhydride (20.3 mg, 1.2 eq) at room temperature. The progress of the reaction was monitored by TLC. Upon completion, the reaction mixture was diluted with 0.8 ml of CHCl$_3$ and 2.4 ml of THF, followed by treatment with N-hydroxysuccinimide (27.3 mg, 1.5 eq) and PS-carbodiimide resin (1.1 mmol/g, 157 mg, 1.5 eq). The progress of the reaction was monitored by TLC. The reaction mixture was filtered, concentrated and purified by flash chromatography on silica gel (ethyl acetate: hexanes=1:1) to give 26.8 mg of activated ester 75 (67% yield for the two steps). $^1$H NMR (500 MHz, CDCl$_3$) δ 6.67-6.73 (m, 3H), 5.92 (d, 2H, J=4 Hz), 4.62-4.71 (m, 2H), 3.74 (s, 3H), 3.64 (brs, 1H), 3.41 (dd, 1H, J=5.8 Hz, 15.8 Hz), 3.29 (dd, 1H, J=4.3 Hz, 16 Hz), 2.77 (br s, 4H), 2.38 (d, 3H, J=2 Hz); $^{13}$C NMR (125 Hz, CDCl$_3$), δ 176.90, 168.56, 165.87, 164.07, 156.41, 148.00, 147.07, 130.11, 120.57, 108.30, 107.79, 104.94, 101.09, 51.08, 43.60, 42.57, 31.29, 25.46, 12.79; MS (APCI) calculated for C$_{21}$H$_{20}$N$_2$O$_9$ 444.12 (M$^+$), found 445.0 (M+H)

Example 7

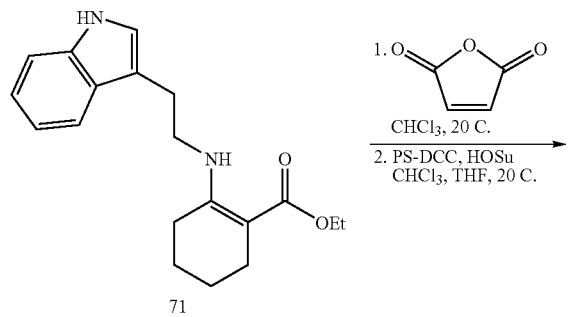

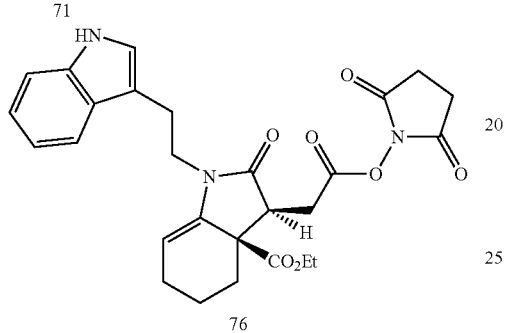

The title compound was prepared in 84% yield according to General Protocol H. $^1$H NMR (500 MHz, CDCl$_3$) δ 8.22 (br s, 1H), 7.64 (d, 1H, J=7.5 Hz), 7.36 (d, 1H, J=8 Hz), 7.17-7.20 (m, 1H), 7.11-7.14 (m, 1H), 7.08 (d, 1H, J=2 Hz), 5.11 (m, 1H), 4.12-4.21 (m, 2H), 3.97-4.03 (m, 1H), 3.55-3.60 (m, 1H), 3.26 (dd, 1H, J=5 Hz, 17.5 Hz), 2.93-3.16 (m, 3H), 2.81 (br s, 4H), 2.66-2.68 (m, 1H), 2.60 (dd, 1H, J=9.5 Hz, 17.5 Hz), 2.25-2.31 (m, 1H), 2.10-2.16 (m, 1H), 1.85-1.89 (m, 1H), 1.48-1.60 (m, 2H), 1.23 (t, 3H, J=7.8 Hz). $^{13}$C NMR (125 MHz, CDCl$_3$) δ 171.33, 171.22, 168.80, 167.38, 138.00, 136.19, 127.29, 121.97, 119.31, 118.57, 112.65, 111.19, 101.00, 61.55, 52.32, 47.28, 40.84, 30.57, 28.58, 25.51, 22.75, 22.36, 19.60, 14.04; MS (APCI) calculated for C$_{27}$H$_{29}$N$_3$O$_7$ 507.20 (M$^+$), found 508.1 (M+H).

Example 8

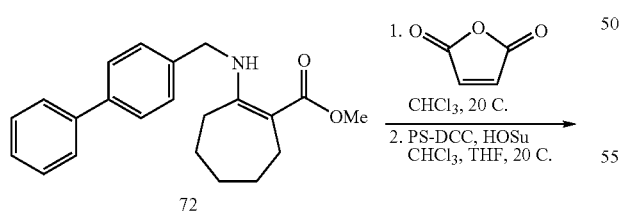

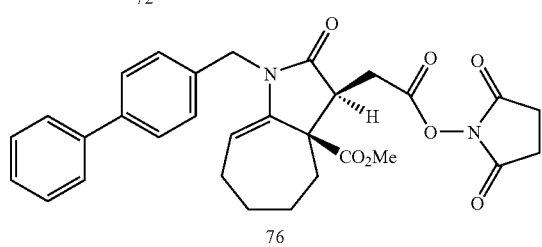

The title compound was prepared in 63% yield according to General Protocol H. $^1$H NMR (500 MHz, CDCl$_3$) δ 7.54-7.59 (m, 4H), 7.41-7.44 (m, 2H), 7.30-7.35 (m, 3H), 5.16 (dd, 1H, J=4 Hz, 9 Hz), 4.85 (d, 1H, J=15.5 Hz), 4.68 (d, 1H, J=15.5 Hz), 3.77 (s, 3H), 3.29 (dd, 1H, J=5.5 Hz, 17.5 Hz), 3.21-3.24 (m, 1H), 2.84 (s, 4H), 2.60-2.84 (m, 2H), 2.12-2.18 (m, 1H), 1.85-1.94 (m, 2H), 1.61-1.72 (m, 3H), 1.19-1.22 (m, 1H); $^{13}$C NMR (125 MHz, CDCl$_3$) δ 171.88, 171.12, 168.72, 167.22, 142.38, 140.68, 140.14, 134.54, 128.71, 127.35, 127.23, 127.18, 126.98, 106.05, 55.68, 52.33, 48.07, 44.03, 36.13, 29.32, 27.68, 27.19, 26.03, 25.55.

Example 9

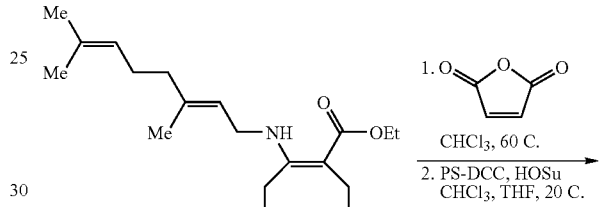

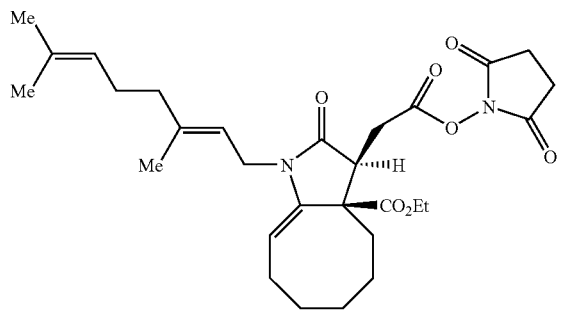

The title compound was prepared in 87% yield according to General Protocol H. $^1$H NMR (500 MHz, CDCl$_3$) δ 4.98-5.06 (m, 2H), 4.80 (dd, 1H, J=8 Hz, 5.3 Hz), 4.18-4.28 (m, 3H), 4.07 (dd, 1H, J=6.5 Hz, 7.8 Hz), 4.20 (dd, 1H, J=5 Hz, 9 Hz), 3.02 (dd, 1H, J=4.8 Hz, 4.3 Hz), 4.81 (br s, 4H), (dd, 1H, J=8.8 Hz, 8.9 Hz), 2.59-2.63 (m, 1H), 1.96-2.08 (m, 7H), 1.55-1.74 (m, 15H), 1.36-1.46 (m, 2H), 1.25 (t, 3H, J=7 Hz); $^{13}$C NMR (125 MHz, CDCl$_3$) δ 171.33, 171.17, 168.66, 167.25, 140.44, 139.24, 131.66, 123.73, 118.09, 103.28, 61.63, 53.63, 47.92, 39.34, 39.13, 38.67, 29.53, 27.96, 26.31, 25.81, 25.62, 25.50, 22.96, 22.58, 17.62, 16.47, 13.98.

Example 10

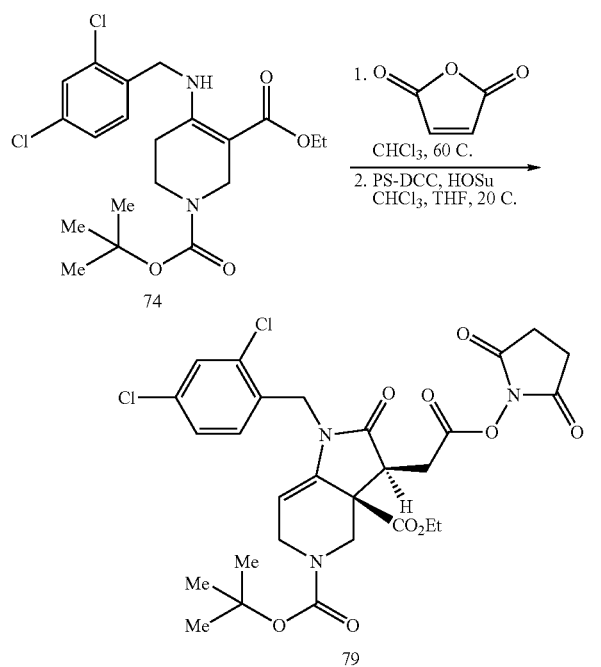

The title compound was prepared according to General Protocol H. Due to the low stability, this activated ester was used directly for the next amidation step.

General Protocol I: Amine Condensation

Example 11

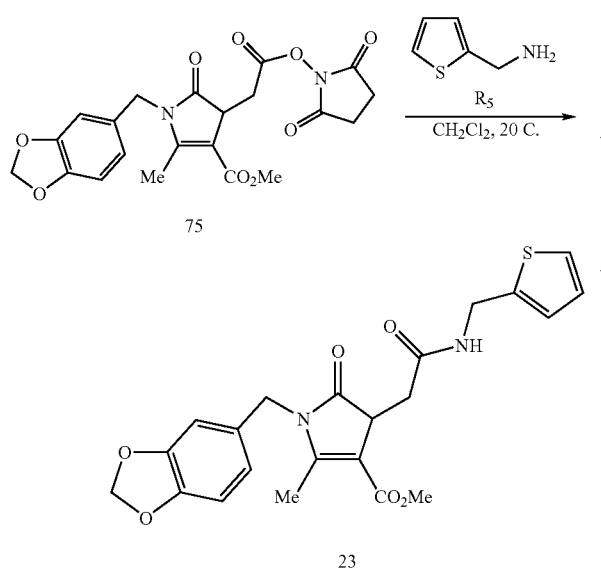

Activated ester 75 (26.8 mg, 60.3 mmol) was dissolved in $CH_2Cl_2$ (0.5 ml) and treated with amine $R_5$ (8.2 mg, 7.4 μl, 1.2 eq). The reaction mixture was kept at room temperature for 2 h, concentrated under reduced pressure and purified by flash chromatography on silica gel (ethyl acetate:hexanes=1:1) to give amide 23 in 82% (21.9 mg) yield. $^1$H NMR (500 MHz, $CDCl_3$) δ 7.18-7.19 (m, 1H), 6.90-6.92 (m, 2H), 6.70-6.77 (m, 3H), 6.26 (br s, 1H), 5.93 (s, 2H), 4.69 (d, 1H, J=15.5 Hz), 4.64 (d, 1H, J=16 Hz), 4.59 (dd, 1H, J=6 Hz, 7.8 Hz), 4.49 (dd, 1H, J=5.3 Hz, 7.5 Hz), 3.68 (s, 3H), 3.50-3.53 (m, 1H), 2.98 (dd, 1H, J=3.8 Hz, 7.1 Hz), 2.93 (dd, 1H, J=6 Hz, 7.5 Hz), 2.31 (d, 3H, J=2 Hz); $^{13}$C NMR (125 MHz, $CDCl_3$) δ 178.62, 169.17, 164.52, 154.93, 148.08, 147.03, 140.83, 130.18, 126.75, 125.93, 125.01, 120.15, 108.31, 107.51, 106.19, 101.07, 50.90, 43.56, 43.39, 38.05, 35.58, 12.89; MS (APCI) calculated for $C_{22}H_{22}N_2O_6S$ 442.48 ($M^+$), found 443.0 (M+H).

Example 12

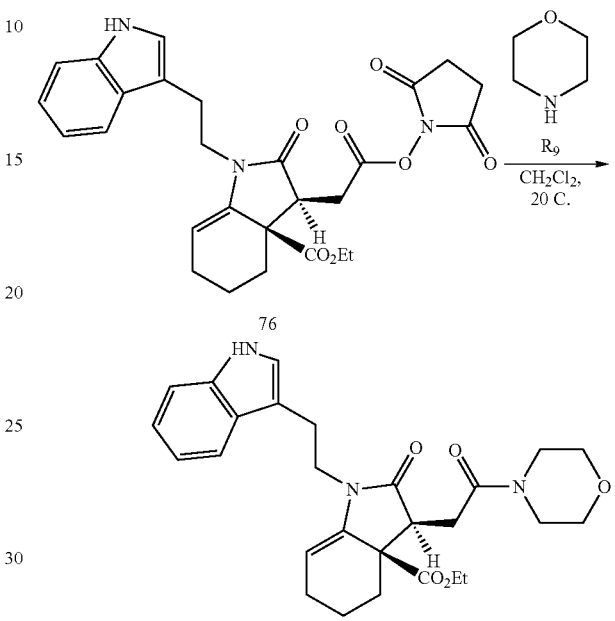

The title compound was prepared in 82% yield according to General Protocol I. $^1$H NMR (500 MHz, $CDCl_3$) δ 8.29-8.33 (br, 1H), 7.66 (d, 1H, J=7.5 Hz), 7.36 (d, 1H, J=8 Hz), 7.19 (t, 1H, J=7.5 Hz), 7.13 (t, 1H, J=7.3 Hz), 7.08 (s, 1H), 5.11 (t, 1H, J=3.5 Hz), 4.08 (q, 2H, J=7 Hz), 3.98-4.04 (m, 1H), 3.54-3.70 (m, 7H), 3.42-3.45 (m, 2H), 3.28 (dd, 1H, J=4.8 Hz), 3.07-3.14 (m, 1H), 2.97-3.02 (m, 1H), 2.88 (dd, 1H, J=4.5 Hz, 8.3 Hz), 2.61-2.63 (m, 1H), 2.22-2.27 (m, 2H), 2.13-2.17 (m, 1H), 1.83-1.87 (m, 1H), 1.50-1.60 (m, 2H), 1.19 (t, 3H, J=7.3 Hz); $^{13}$C NMR (125 MHz, $CDCl_3$) δ 173.48, 172.06, 168.96, 138.46, 136.20, 127.29, 121.96, 121.85, 119.29, 118.59, 112.75, 111.15, 100.39, 66.76, 66.40, 61.05, 52.51, 47.54, 45.77, 42.27, 40.60, 30.71, 29.58, 22.84, 22.36, 19.69, 14.13; MS (APCI) calculated for $C_{27}H_{33}N_3O_5$ 479.57 ($M^+$), found 480.1 (M+H).

Example 13

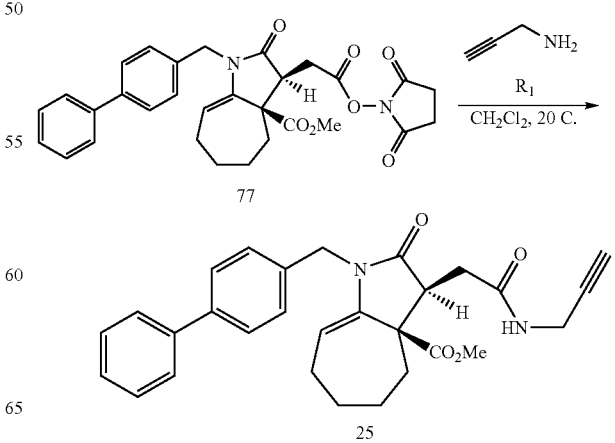

25

The title compound was prepared in quantitative yield according to General Protocol I. $^1$H NMR (500 MHz, CDCl$_3$) δ 7.54-7.59 (m, 4H), 7.42-7.45 (m, 2H), 7.31-7.36 (m, 3H), 5.14 (dd, 1H, J=4.5 Hz, 9 Hz), 4.86 (d, 1H, J=16 Hz), 4.63 (d, 1H, J=16 Hz), 4.11 (ddd, 1H, J=2.5 Hz, 2.8 Hz, 8.8 Hz), 4.02 (ddd, 1H, J=2.5 Hz, 2.5 Hz, 8.8 Hz), 3.66 (s, 3H), 3.11 (dd, 1H, J=4.8 Hz, 8.3 Hz), 2.62 (dd, 1H, J=8.3 Hz, 15.3 Hz), 2.47-2.52 (m, 1H), 2.27 (dd, 1H, J=4.8 Hz, 15.3 Hz), 2.22 (t, J=2.5 Hz), 1.48-1.88 (m, 6H), 1.25-1.32 (m, 1H); $^{13}$C NMR (125 MHz, CDCl$_3$) δ 174.34, 171.22, 170.21, 142.26, 140.64, 140.25, 134.58, 128.75, 127.45, 127.30, 127.18, 126.99, 105.95, 79.53, 71.38, 55.52, 52.08, 48.89, 43.98, 35.17, 33.46, 29.31, 27.20, 27.07, 25.99; MS (APCI) calculated for C$_{29}$H$_{30}$N$_2$O$_4$ 470.56 (M$^+$), found 471.1 (M+H).

Example 14

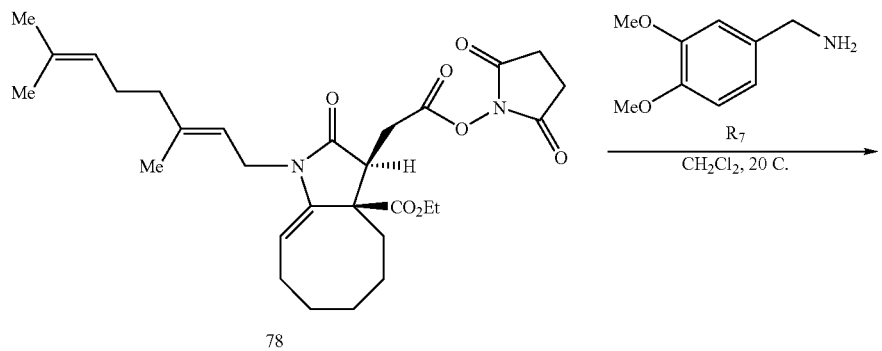

78

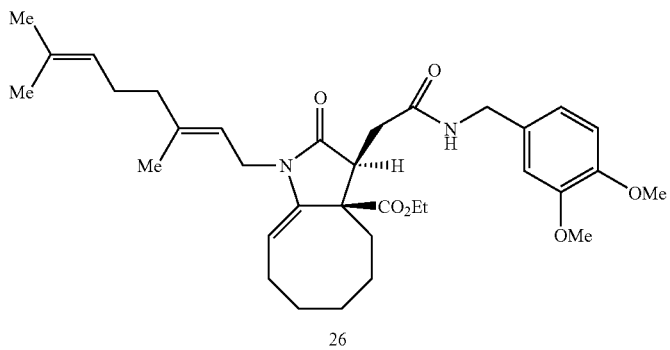

26

The title compound was prepared in 92% yield according to General Procedure I. $^1$H NMR (500 MHz, CDCl$_3$) δ 7.21 (br, 1H), 6.87 (s, 1H), 6.78-6.87 (m, 2H), 5.02-5.05 (m, 1H), 4.97-4.99 (m, 1H), 4.80 (t, 1H, J=9 Hz), 4.36 (d, 2H, J=2.8 Hz), 4.08-4.13 (m, 4H), 3.87 (s, 3H), 3.84 (s, 3H), 2.97 (dd, 1H, J=4.5 Hz, 4.3 Hz), 2.64 (dd, 1H, J=8.5 Hz, 7.8 Hz), 2.53-2.58 (m, 1H), 2.16 (dd, 1H, J=4.5 Hz, 7.8 Hz), 2.01-2.05 (m, 4H), 1.96-1.99 (m, 2H), 1.57-1.69 (m, 14H), 1.36-1.48 (m, 2H), 1.20 (t, 3H, J=2.3 Hz); $^{13}$C NMR (125 MHz, CDCl$_3$) δ173.74, 171.39, 170.42, 149.02, 148.20, 140.32, 139.17, 131.66, 130.97, 123.67, 119.88, 118.01, 111.06, 111.01, 103.65, 61.20, 55.84, 55.81, 54.41, 47.85, 43.46, 39.34, 38.49, 37.19, 34.55, 27.72, 26.37, 26.28, 25.61, 22.97, 22.34, 17.60, 16.40, 14.00. MS (APCI) calculated for C$_{34}$H$_{48}$N$_2$O$_6$ 580.75 (M$^+$), found 581.3 (M+H).

Example 15

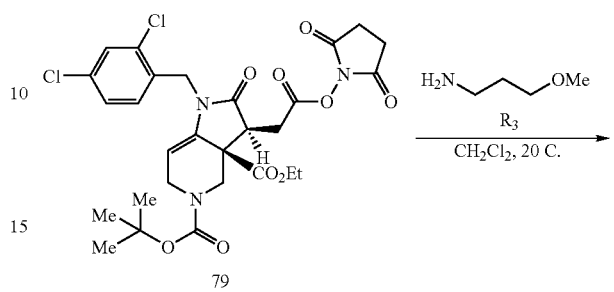

79

-continued

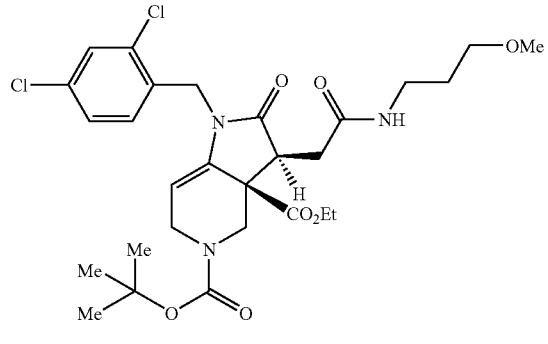

27

The title compound was prepared in 65% yield according to General Protocol I. ¹H NMR (500 MHz, C₆D₆, 343K) δ 7.43 (d, 1H, J=8 Hz), 7.24-7.25 (m, 1H), 7.04-7.06 (m, 1H), 5.59 (br, 1H), 5.26 (d, 1H, J=12.5 Hz), 4.95 (d, 1H, J=17 Hz), 4.49 (t, 1H, J=3.3 Hz), 4.42 (d, 1H, J=16.5 Hz), 4.25 (br, 1H), 3.91-4.01 (m, 2H), 3.46 (dd, 1H, J=3.5 Hz, 18 Hz), 3.34-3.38 (m, 2H), 3.26-3.28 (m, 2H), 3.26-3.28 (m, 3H), 2.93 (dd, 1H, J=4.8 Hz, 7.9 Hz), 2.79 (d, 1H, J=13 Hz), 2.23 (dd, 1H, J=8.8 Hz, 7.9 Hz), 1.67-1.70 (m, 2H), 1.55 (s, 9H), 1.02 (t, 3H, J=7.3 Hz); ¹³C NMR (125 MHz, C₆D₆, 343K) δ 173.97, 170.14, 169.53, 154.51, 138.40, 134.12, 133.86, 132.57, 130.15, 129.40, 129.11, 127.91, 96.84, 79.49, 71.27, 61.28, 58.31, 53.37, 48.19, 45.37, 42.28, 41.46, 38.11, 33.48, 30.09, 29.87, 28.51, 14.06; MS (APCI) calculated for C₂₈H₃₇Cl₂N₃O₇ 597.20 (M⁺), found 634.0 (M+Cl)

Example 16

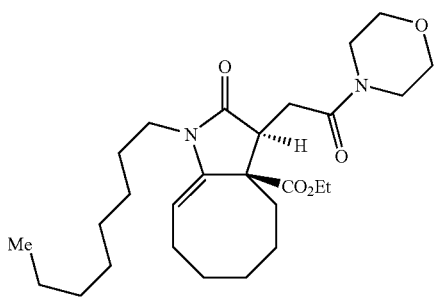

Pyrrolidinone 28. The title compound (51 mg) was prepared according to General Protocols G, H and 1, followed by purification by flash chromatography on silica gel. ¹H NMR (500 MHz, CD₃OD) δ 4.80 (dd, 1H, J=3 Hz, 7.5 Hz), 4.03-4.19 (m, 2H), 3.62-3.69 (m, 5H), 3.34-3.55 (m, 5H), 3.21 (dd, 1H, J=4 Hz, 4.5 Hz), 2.79 (dd, 1H, J=12.5 Hz, 4.5 Hz), 2.65-2.69 (m, 1H), 2.40 (dd, 1H, J=8 Hz, 8.5 Hz), 1.96-2.08 (m, 2H), 1.36-1.76 (m, 8H), 1.17-1.28 (m, 14H), 0.86 (t, 3H, J=6.75 Hz); ¹³C NMR (125 MHz, d⁶-DMSO) δ 173.77, 172.16, 168.98, 141.38, 101.88, 66.76, 66.43, 65.79, 61.02, 53.95, 48.45, 45.73, 42.18, 40.14, 31.70, 31.50, 29.19, 29.12, 28.27, 26.86, 26.06, 25.79, 22.97, 22.85, 22.57, 15.21, 14.02; MS (APCI) calculated for C₂₇H₄₄N₂O₅ 476.33 (M⁺), found 477.2 (M+H).

Example Compounds from The Pyrrolidinone Library

Example 17

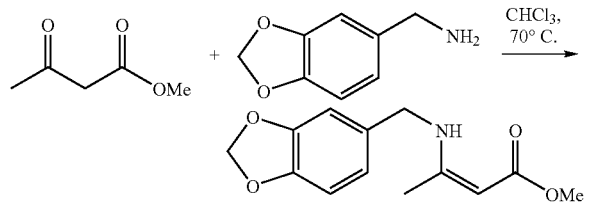

This compound was prepared in about 90% yield. ¹H NMR (400 MHz, CDCl₃) δ 8.85 (br, 1H), 6.69-6.77 (m, 3H), 4.93 (s, 2H), 4.52 (s, 1H), 4.31 (d, 2H, J=6.4 Hz), 3.62 (s, 3H), 1.91 (s, 3H); ¹³C NMR (125 MHz, CDCl₃), δ 170.82, 161.71, 148.03, 146.85, 132.48, 119.91, 108.36, 107.36, 101.03, 82.76, 49.94, 46.58, 19.31.

Example 18

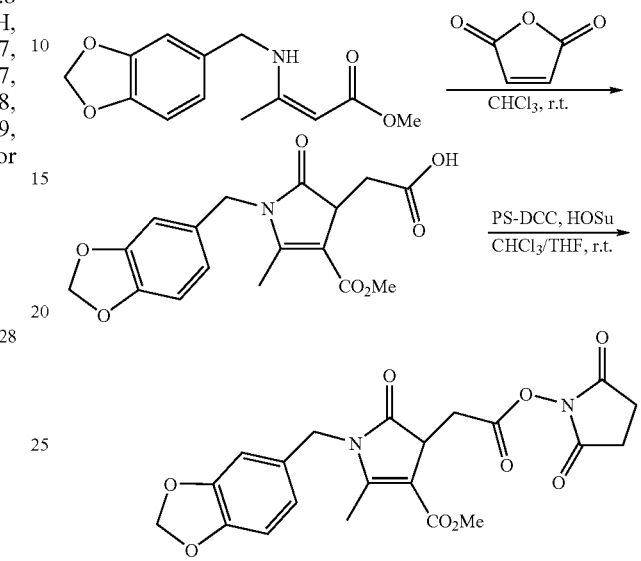

This compound was prepared in about 67% yield. ¹H NMR (500 MHz, CDCl₃) δ 6.67-6.73 (m, 3H), 5.92 (d, 2H, J=4 Hz), 4.62-4.71 (m, 2H), 3.74 (s, 3H), 3.64 (br s, 1H), 3.41 (dd, 1H, J=5.8 Hz, 15.8 Hz), 3.29 (dd, 1H, J=4.3 Hz, 16 Hz), 2.77 (brs, 4H), 2.38 (d, 3H, J=2 Hz); ¹³C NMR (125 Hz, CDCl₃), δ 176.90, 168.56, 165.87, 164.07, 156.41, 148.00, 147.07, 130.11, 120.57, 108.30, 107.79, 104.94, 101.09, 51.08, 43.60, 42.57, 31.29, 25.46, 12.79.

Example 19

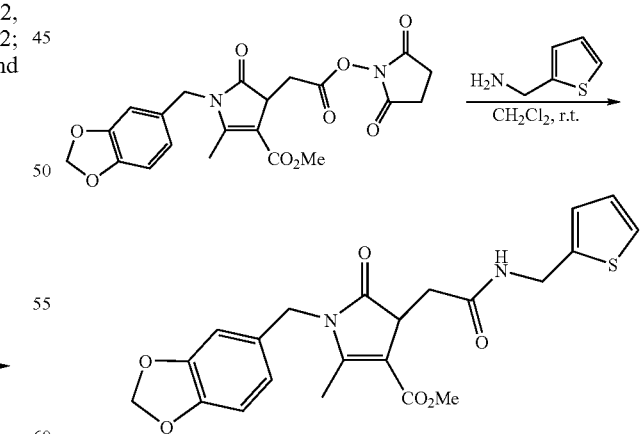

This compound was prepared in about 82% yield. ¹H NMR (500 MHz, CDCl₃), 7.18-7.19 (m, 1H), 6.90-6.92 (m, 2H), 6.70-6.77 (m, 3H), 6.26 (br s, 1H), 5.93 (s, 2H), 4.69 (d, 1H, J=15.5 Hz), 4.64 (d, 1H, J=16 Hz), 4.59 (dd, 1H, J=6 Hz, 7.8 Hz), 4.49 (dd, 1H, J=5.3 Hz, 7.5 Hz), 3.68 (s, 3H), 3.50-3.53 (m, 1H), 2.98 (dd, 1H, J=3.8 Hz, 7.1 Hz), 2.93 (dd, 1H, J=6

Hz, 7.5 Hz), 2.31 (d, 3H, J=2 Hz); $^{13}$C NMR (125 MHz, CDCl$_3$) δ 178.62, 169.17, 164.52, 154.93, 148.08, 147.03, 140.83, 130.18, 126.75, 125.93, 125.01, 120.15, 108.31, 107.51, 106.19, 101.07, 50.90, 43.56, 43.39, 38.05, 35.58, 12.89; MS (CI) calcd for C$_{22}$H$_{22}$N$_2$O$_6$S 442.48, found 443.0.

Example 20

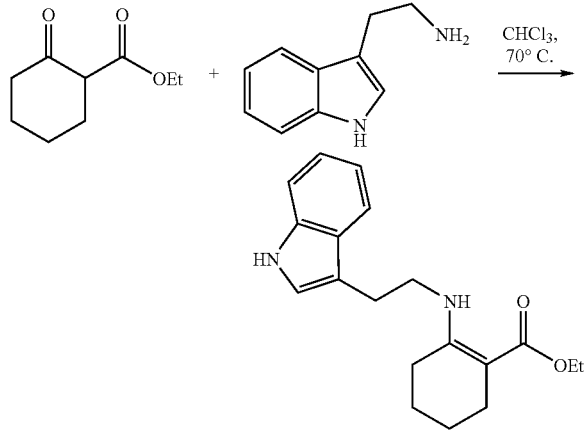

This compound was prepared in about 84% yield. $^1$H NMR (500 MHz, CDCl$_3$) δ 9.07 (br s, 1H), 8.16 (br s, 1H), 7.58 (d, 1H, J=7.5 Hz), 7.33 (d, 1H, J=8 Hz), 7.20 (t, 1H, J=7 Hz), 7.13 (t, 1H, J=7.5 Hz), 7.04 (d, 1H, J=2.5 Hz), 4.14 (q, 2H, J=7.2 Hz), 3.49 (dt, 2H, J=7 Hz, 6 Hz), 3.02 (t, 2H, J=7.3 Hz), 2.28-2.30 (m, 4H), 1.61-1.63 (m, 2H), 1.54-1.57 (m, 2H), 1.28 (t, 3H, J=7 Hz); $^{13}$C NMR (125 MHz, CDCl$_3$) δ 170.88, 159.51, 136.26, 127.15, 122.21, 121.91, 119.22, 118.50, 112.89, 111.20, 89.36, 58.58, 42.81, 26.52, 26.43, 23.80, 22.66, 22.25, 14.65.

Example 21

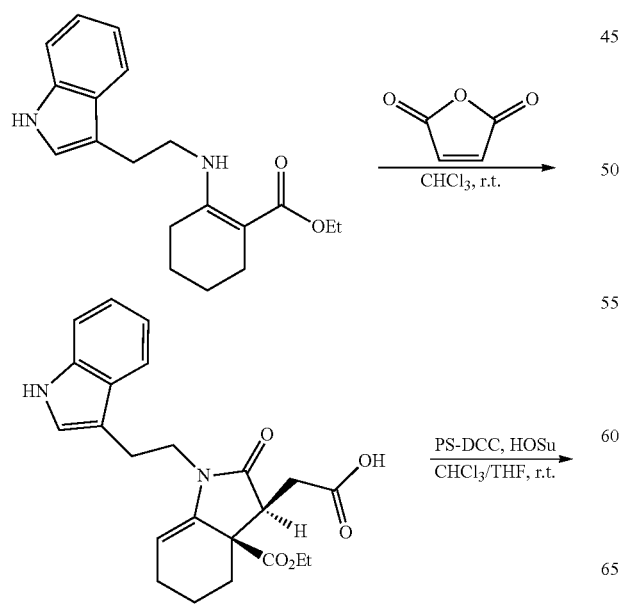

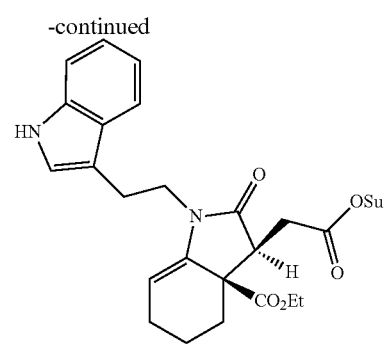

This compound was prepared in about 84% yield. $^1$H NMR (500 MHz, CDCl$_3$) δ 8.22 (br s, 1H), 7.64 (d, 1H, J=7.5 Hz), 7.36 (d, 1H, J=8 Hz), 7.17-7.20 (m, 1H), 7.11-7.14 (m, 1H), 7.08 (d, 1H, J=2 Hz), 5.11 (m, 1H), 4.12-4.21 (m, 2H), 3.97-4.03 (m, 1H), 3.55-3.60 (m, 1H), 3.26 (dd, 1H, J=5 Hz, 17.5 Hz), 2.93-3.16 (m, 3H), 2.81 (brs, 4H), 2.66-2.68 (m, 1H), 2.60 (dd, 1H, J=9.5 Hz, 17.5 Hz), 2.25-2.31 (m, 1H), 2.10-2.16 (m, 1H), 1.85-1.89 (m, 1H), 1.48-1.60 (m, 2H), 1.23 (t, 3H, J=7.8 Hz). $^{13}$C NMR (125 MHz, CDCl$_3$) δ 171.33, 171.22, 168.80, 167.38, 138.00, 136.19, 127.29, 121.97, 119.31, 118.57, 112.65, 111.19, 101.00, 61.55, 52.32, 47.28, 40.84, 30.57, 28.58, 25.51, 22.75, 22.36, 19.60, 14.04.

Example 22

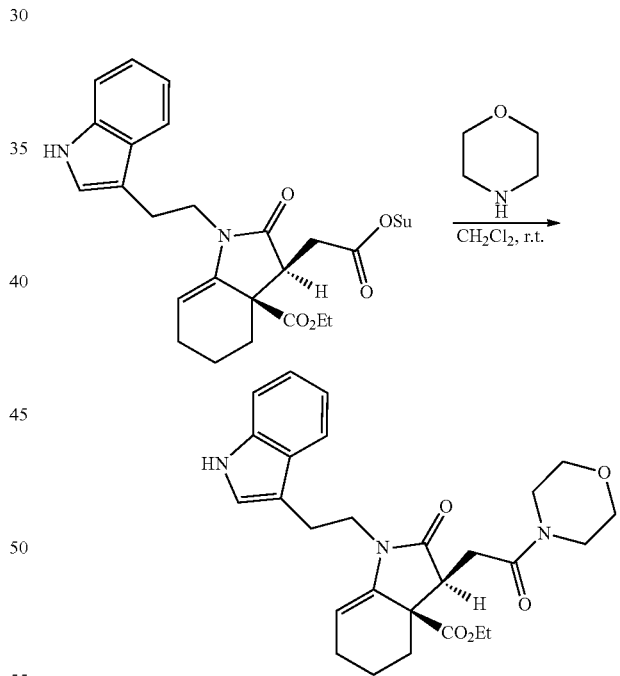

This compound was prepared in about 82% yield. $^1$H NMR (500 MHz, CDCl$_3$) δ 8.29-8.33 (br, 1H), 7.66 (d, 1H, 7.5 Hz), 7.36 (d, 1H, J=8 Hz), 7.19 (t, 1H, J=7.5 Hz), 7.13 (t, 1H, J=7.3 Hz), 7.08 (s, 1H), 5.11 (t, 1H, J=3.5 Hz), 4.08 (q, 2H, J=7 Hz), 3.98-4.04 (m, 1H), 3.54-3.70 (m, 7H), 3.42-3.45 (m, 2H), 3.28 (dd, 1H, J=4.8 Hz), 3.07-3.14 (m, 1H), 2.97-3.02 (m, 1H), 2.88 (dd, 1H, J=4.5 Hz, 8.3 Hz), 2.61-2.63 (m, 1H), 2.22-2.27 (m, 2H), 2.13-2.17 (m, 1H), 1.83-1.87 (m, 1H), 1.50-1.60 (m, 2H), 1.19 (t, 3H, J=7.3 Hz); $^{13}$C NMR (125 MHz, CDCl$_3$) δ 173.48, 172.06, 168.96, 138.46, 136.20, 127.29, 121.96, 121.85, 119.29, 118.59, 112.75, 111.15, 100.39, 66.76, 66.40, 61.05, 52.51, 47.54, 45.77, 42.27, 40.60, 30.71, 29.58, 22.84, 22.36, 19.69, 14.13; MS (CI) calcd for $C_{27}H_{33}N_3O_5$ 479.57, found 480.1.

Example 23

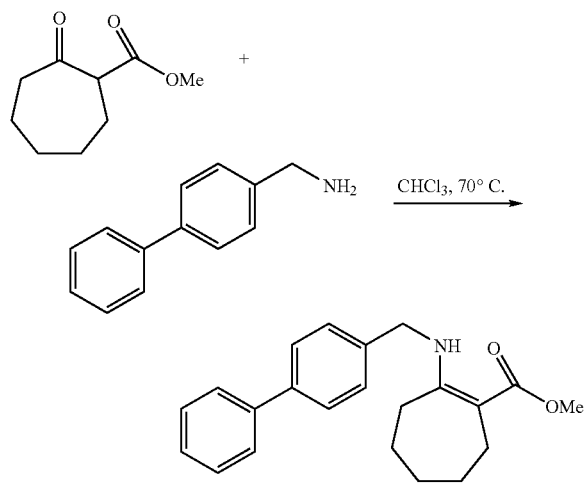

This compound was prepared in about 79% yield. $^1$H NMR (500 MHz, CDCl$_3$) δ 9.72 (br s, 1H), 7.57-7.60 (m, 4H), 7.43-7.46 (m, 2H), 7.34-7.36 (m, 3H), 4.50 (d, 2H, J=6.5 Hz), 3.69 (s, 3H), 2.48-2.53 (m, 4H), 1.68-1.70 (m, 2H), 1.45-1.50 (m, 4H); $^{13}$C NMR (125 MHz, CDCl$_3$) δ 171.00, 167.45, 140.71, 140.04, 138.69, 128.72, 127.34, 127.21, 127.17, 126.99, 95.07, 50.40, 46.58, 31.78, 28.74, 28.34, 25.86, 25.02.

Example 24

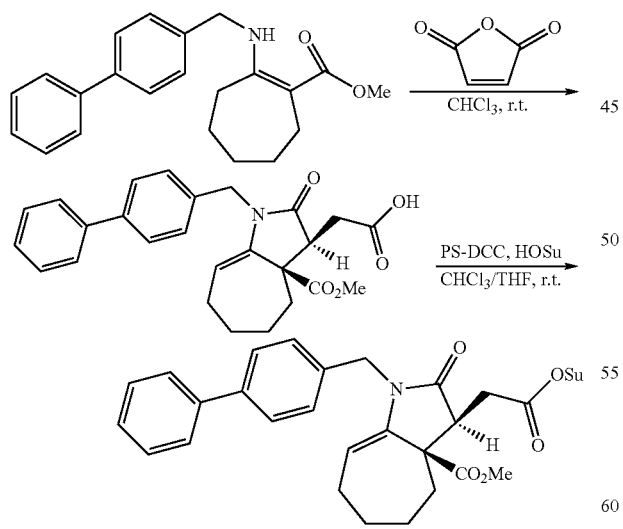

This compound was prepared in about 63% yield. $^1$H NMR (500 MHz, CDCl$_3$) δ 7.54-7.59 (m, 4H), 7.41-7.44 (m, 2H), 7.30-7.35 (m, 3H), 5.16 (dd, 1H, J=4 Hz, 9 Hz), 4.85 (d, 1H, J=15.5 Hz), 4.68 (d, 1H, J=15.5 Hz), 3.77 (s, 3H), 3.29 (dd, 1H, J=5.5 Hz, 17.5 Hz), 3.21-3.24 (m, 1H), 2.84 (s, 4H), 2.60-2.84 (m, 2H), 2.12-2.18 (m, 1H), 1.85-1.94 (m, 2H), 1.61-1.72 (m, 3H), 1.19-1.22 (m, 1H); $^{13}$C NMR (125 MHz, CDCl$_3$) δ 171.88, 171.12, 168.72, 167.22, 142.38, 140.68, 140.14, 134.54, 128.71, 127.35, 127.23, 127.18, 126.98, 106.05, 55.68, 52.33, 48.07, 44.03, 36.13, 29.32, 27.68, 27.19, 26.03, 25.55.

Example 25

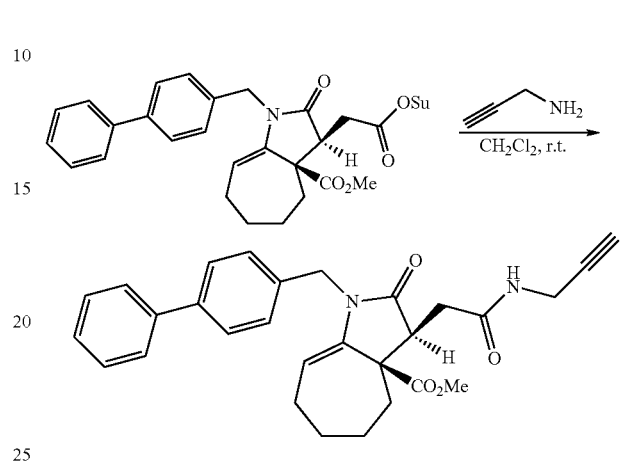

This compound was prepared in quantitative yield. $^1$H NMR (500 MHz, CDCl$_3$) δ 7.54-7.59 (m, 4H), 7.42-7.45 (m, 2H), 7.31-7.36 (m, 3H), 5.14 (dd, 1H, J=4.5 Hz, 9 Hz), 4.86 (d, 1H, J=16 Hz), 4.63 (d, 1H, J=16 Hz), 4.11 (ddd, 1H, J=2.5 Hz, 2.8 Hz, 8.8 Hz), 4.02 (ddd, 1H, J=2.5 Hz, 2.5 Hz, 8.8 Hz), 3.66 (s, 3H), 3.11 (dd, 1H, J=4.8 Hz, 8.3 Hz), 2.62 (dd, 1H, J=8.3 Hz, 15.3 Hz), 2.47-2.52 (m, 1H), 2.27 (dd, 1H, J=4.8 Hz, 15.3 Hz), 2.22 (t, J=2.5 Hz), 1.48-1.88 (m, 6H), 1.25-1.32 (m, 1H); $^{13}$C NMR (125 MHz, CDCl$_3$) δ 174.34, 171.22, 170.21, 142.26, 140.64, 140.25, 134.58, 128.75, 127.45, 127.30, 127.18, 126.99, 105.95, 79.53, 71.38, 55.52, 52.08, 48.89, 43.98, 35.17, 33.46, 29.31, 27.20, 27.07, 25.99; MS (CI) calcd for $C_{29}H_{30}N_2O_4$ 470.56, found 471.1.

Example 26

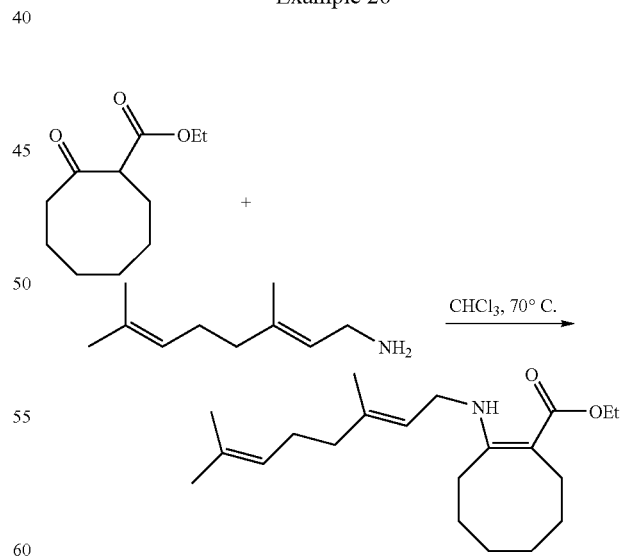

This compound was prepared in about 57% yield. $^1$H NMR (400 MHz, CDCl$_3$) δ 9.15 (br s, 1H), 5.24-5.26 (m, 1H), 5.07-5.09 (m, 1H), 4.10 (q, 2H, J=7.1 Hz), 3.79-3.82 (m, 2H), 2.48-2.51 (m, 2H), 2.40 (br, 2H), 2.05-2.10 (m, 2H), 1.98-2.01 (m, 2H), 1.59-1.67 (m, 11H), 1.45-1.50 (m, 6H), 1.24 (t, J=7 Hz). $^{13}$C NMR (100 MHz, CDCl$_3$) δ 170.70, 163.20, 138.33, 131.66, 123.88, 121.55, 91.74, 58.42, 40.88, 39.46, 30.62, 28.58, 26.71, 26.34, 26.25, 25.66, 25.51, 17.68, 16.30, 14.70.

Example 27

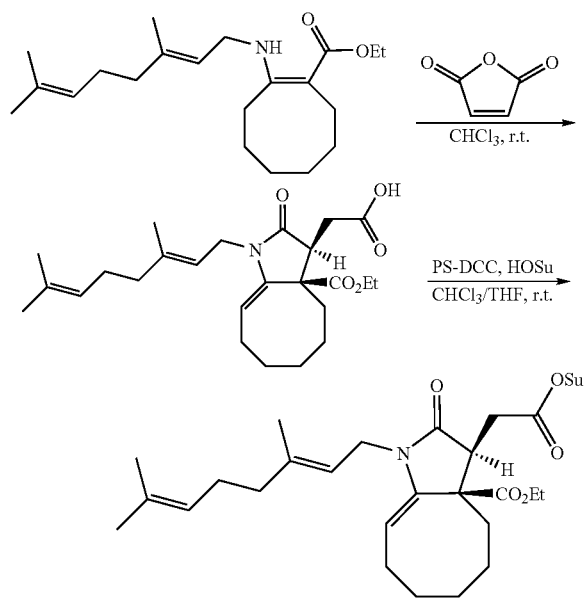

This compound was prepared in about 87%. $^1$H NMR (500 MHz, CDCl$_3$) δ 4.98-5.06 (m, 2H), 4.80 (dd, 1H, J=8 Hz, 5.3 Hz), 4.18-4.28 (m, 3H), 4.07 (dd, 1H, J=6.5 Hz, 7.8 Hz), 4.20 (dd, 1H, J=5 Hz, 9 Hz), 3.02 (dd, 1H, J=4.8 Hz, 4.3 Hz), 4.81 (br s, 4H), (dd, 1H, J=8.8 Hz, 8.9 Hz), 2.59-2.63 (m, 1H), 1.96-2.08 (m, 7H), 1.55-1.74 (m, 15H), 1.36-1.46 (m, 2H), 1.25 (t, 3H, J=7 Hz); $^{13}$C NMR (125 MHz, CDCl$_3$) 171.33, 171.17, 168.66, 167.25, 140.44, 139.24, 131.66, 123.73, 118.09, 103.28, 61.63, 53.63, 47.92, 39.34, 39.13, 38.67, 29.53, 27.96, 26.31, 25.81, 25.62, 25.50, 22.96, 22.58, 17.62, 16.47, 13.98.

Example 28

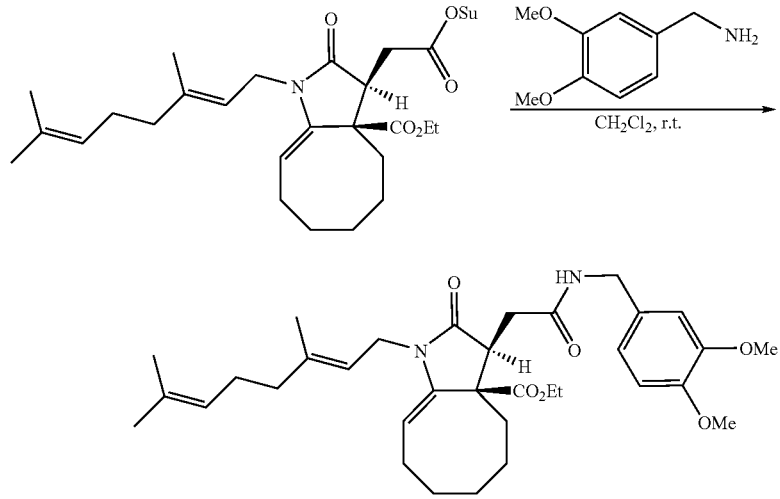

This compound was prepared in about 92% yield according to General Procedure C. $^1$H NMR (500 MHz, CDCl$_3$) δ 7.21 (br, 1H), 6.87 (s, 1H), 6.78-6.87 (m, 2H), 5.02-5.05 (m, 1H), 4.97-4.99 (m, 1H), 4.80 (t, 1H, J=9 Hz), 4.36 (d, 2H, J=2.8 Hz), 4.08-4.13 (m, 4H), 3.87 (s, 3H), 3.84 (s, 3H), 2.97 (dd, 1H, J=4.5 Hz, 4.3 Hz), 2.64 (dd, 1H, J=8.5 Hz, 7.8 Hz), 2.53-2.58 (m, 1H), 2.16 (dd, 1H, J=4.5 Hz, 7.8 Hz), 2.01-2.05 (m, 4H), 1.96-1.99 (m, 2H), 1.57-1.69 (m, 14H), 1.36-1.48 (m, 2H), 1.20 (t, 3H, J=2.3 Hz); $^{13}$C NMR (125 MHz, CDCl$_3$) δ 173.74, 171.39, 170.42, 149.02, 148.20, 140.32, 139.17, 131.66, 130.97, 123.67, 119.88, 118.01, 111.06, 111.01, 103.65, 61.20, 55.84, 55.81, 54.41, 47.85, 43.46, 39.34, 38.49, 37.19, 34.55, 27.72, 26.37, 26.28, 25.61, 22.97, 22.34, 17.60, 16.40, 14.00. MS (Cl) calcd for C$_{34}$H$_{48}$N$_2$O$_6$ 580.75, found 581.3.

Example 29

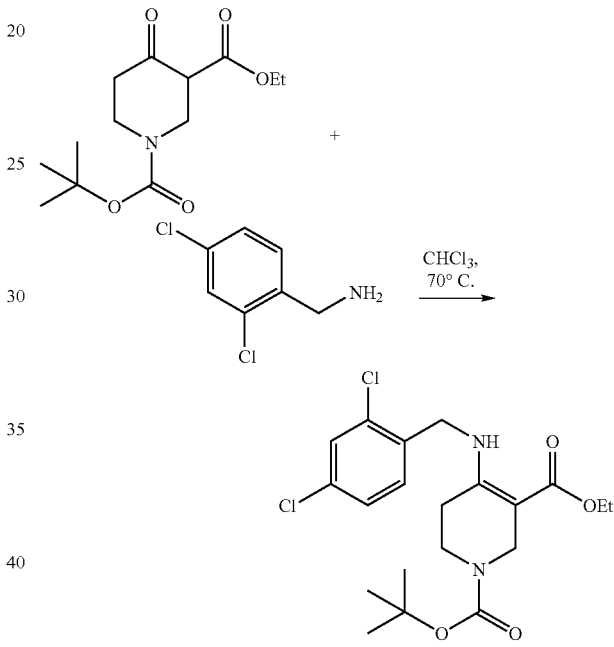

This compound was prepared in about 73% yield. ¹H NMR (CD₃CN, 298 K) δ 9.15 (s, 1H), 7.48 (d, 1H, J=2 Hz), 7.27-7.37 (m, 2H), 4.45 (d, 2H, J=6.5 Hz), 4.10 (q, 2H, J=7 Hz), 4.00 (s, 2H), 3.41 (t, 2H, J=6 Hz), 2.33 (t, 2H, J=6 Hz), 1.43 (s, 9H), 1.22 (t, 3H, J=7.3 Hz).

Example 30

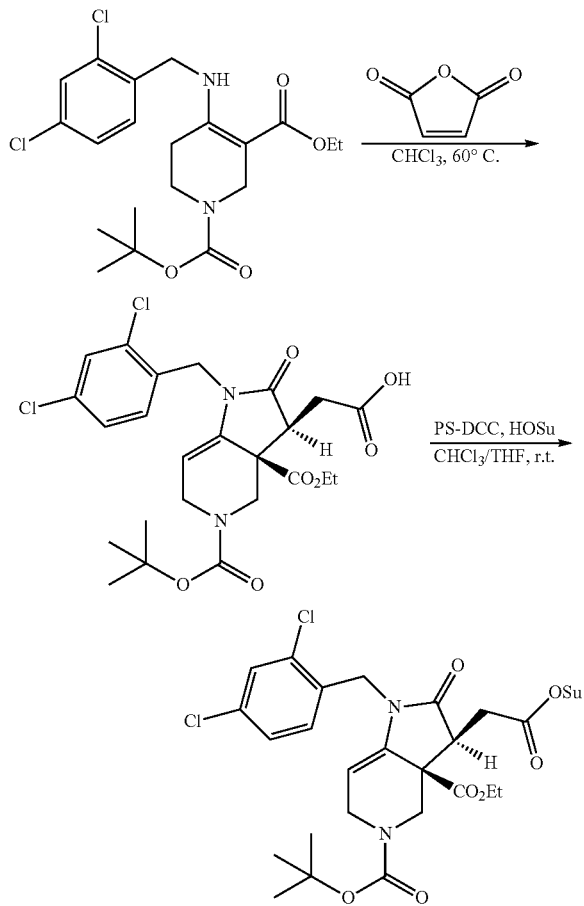

This compound was prepared in about 30% yield and was used directly for next step.

Example 31

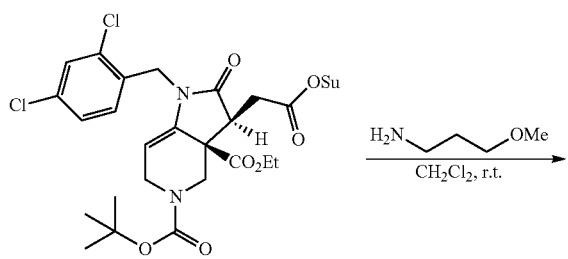

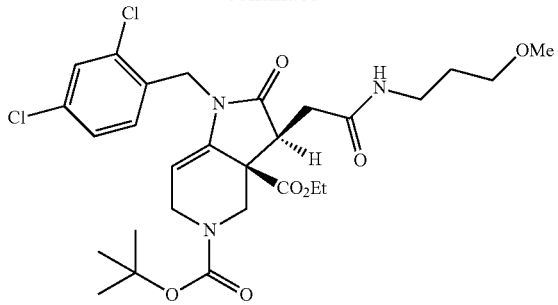

This compound was prepared in about 65% yield according to General Procedure C. ¹H NMR (500 MHz, C₆D₆, 343K) δ 7.43 (d, 1H, J=8 Hz), 7.24-7.25 (m, 1H), 7.04-7.06 (m, 1H), 5.59 (br, 1H), 5.26 (d, 1H, J=12.5 Hz), 4.95 (d, 1H, J=17 Hz), 4.49 (t, 1H, J=3.3 Hz), 4.42 (d, 1H, J=16.5 Hz), 4.25 (br, 1H), 3.91-4.01 (m, 2H), 3.46 (dd, 1H, J=3.5 Hz, 18 Hz), 3.34-3.38 (m, 2H), 3.26-3.28 (m, 2H), 3.26-3.28 (m, 3H), 2.93 (dd, 1H, J=4.8 Hz, 7.9 Hz), 2.79 (d, 1H, J=13 Hz), 2.23 (dd, 1H, J=8.8 Hz, 7.9 Hz), 1.67-1.70 (m, 2H), 1.55 (s, 9H), 1.02 (t, 3H, J=7.3 Hz); ¹³C NMR (125 MHz, C₆D₆, 343K) δ 173.97, 170.14, 169.53, 154.51, 138.40, 134.12, 133.86, 132.57, 130.15, 129.40, 129.11, 127.91, 96.84, 79.49, 71.27, 61.28, 58.31, 53.37, 48.19, 45.37, 42.28, 41.46, 38.11, 33.48, 30.09, 29.87, 28.51, 14.06; MS(Cl) calcd for $C_{28}H_{37}Cl_2N_3O_7$ 597.20, found 634.0 (M+Cl)

Crystal Structure Data Collection. An irregular broken fragment (0.16×0.16×0.16 mm) was selected under a stereomicroscope while immersed in Fluorolube oil to avoid possible reaction with air. The crystal was removed from the oil using a tapered glass fiber that also served to hold the crystal for data collection. The crystal was mounted and centered on a Bruker SMART APEX system at 100 K. Rotation and still images showed the diffractions to be sharp. Frames separated in reciprocal space were obtained and provided an orientation matrix and initial cell parameters. Final cell parameters were obtained from the full data set.

A "full sphere" data set was obtained which samples approximately all of reciprocal space to a resolution of 0.75 Å using 0.3% steps in using 10 second integration times for each frame. Data collection was made at 100 K. Integration of intensities and refinement of cell parameters were done using SAINT [1]. Absorption corrections were applied using SADABS [1] based on redundant diffractions.

Structure solution and refinement. Referring to Table 1, The space group was determined as P1 (bar) based on systematic absences and intensity statistics. Direct methods were used to locate most C atoms and from the E-map. Repeated difference Fourier maps allowed recognition of all expected C, N, and O atoms. Following anisotropic refinement of all non-H atoms, ideal H-atom positions were calculated. Final refinement was anisotropic for all non-H atoms, and isotropic-riding for H atoms. No anomalous bond lengths or thermal parameters were noted. All ORTEP diagrams have been drawn with 50% probability ellipsoids.

Example 32

Dihydroquinolone 29, as described in PCT/US2008/002203 (incorporated herein by reference), was shown to display dose-dependent blockade of ATP synthesis in A549 cells in the presence of glycolytic inhibitor 2-deoxy-glucose and inhibition of NADH oxidation in isolated mitochondria.

Example 33

The tricyclic benzodiazepine library was evaluated for the ability to inhibit growth of A549 cell line (non-small cell lung cancer). The high-throughput cell viability assay was performed with 1000 cells per well using an ATP-monitoring luciferase-based protocol at a 20 µM average concentration of small molecules. This assay resulted in the discovery of a new inhibitor of cell proliferation designated as triazatricyclamide A (top bar in FIG. 5. of PCT/US2008/002203, which is incorporated herein by reference) with $IC_{50}$ values ranging from 161-970 nM.

Chromatin condensation in HL-60 cells treated with triazatricyclamide A was shown to be greater than the DMSO control, which was visualized by staining cells with Hoechst 33342. Time-dependence of caspase-3/7 activation in HL-60 cells treated with triazatricyclamide A showed a steady increase in activity 3 hours through 22 hours after treatment. In contrast, staurosporine treatment increased activity between 3 and 6 hours after treatment, after which activity decreased. Release of ROS in HL-60 cells in response to treatment with triazatricyclamide A was measured by monitoring DHE fluorescence and the time-dependence and effect of z-VAD-fmk on PS exposure and membrane integrity was investigated in HL-60 cells treated with triazatricyclamide A. Jurkat A3 cells lacking key components of the extrinsic apoptotic pathway and MCF7-Fas cells overexpressing $Bcl-x_L$ were treated with triazatricyclamide A, leucine zipper tagged Fas ligand (LzFasL) and DMSO for 24 hours and the extent of DNA fragmentation was measured.

Initial analysis revealed that triazatricyclamide A activated both caspase-dependent and caspase-independent cell death pathways. The early events, such as ROS generation and PS exposure, were found to be highly dependent on caspase activation. It appears, however, that DNA degradation and cell death induced by triazatricyclamide A become at some point independent of caspase activity. A number of caspase independent forms of cell death have been described. Most of them involve release of mitochondrial proteins such as AIF, HtrA2/OMI or ENDO G, which can cause nuclear changes independently of caspase activation. However, the release of such factors would be inhibited by $Bcl-x_L$. Without wishing to be bound by theory, the fact that $Bcl-x_L$ did not prevent cell death, at least not in MCF7 cells, seems to suggest that triazatricyclamide A activated a pathway that was independent of mitochondria, i.e. by causing lysosomal stress. This unique activity profile does not correlate to any previously characterized small-molecule agents that induce either caspase-dependent or caspase-independent cell death.

Example 34

A high-throughput assay was developed for identification of new inhibitors of glycolysis. The effect of the pyrrolidinone library on intracellular ATP level of A549 cells was tested in either the presence or absence of antimycin A (inhibitor of mitochondrial electron-transport chain). The compounds, which showed more pronounced effect on ATP levels in medium containing antimycin A, were considered as potential glycolytic inhibitors. Initial hits were further verified by evaluating their effects on lactate production. Since lactate is a toxic end-product of glycolysis effluxed to the intercellular space, treatment of cells with glycolytic inhibitors should lead to decreased levels of lactate in cell culture medium. The screen resulted in a discovery of novel inhibitors of glycolysis.

Two of these, designated P8A7 and P9E11, suppressed ATP production more efficiently in the presence of antimycin A (10 nM), elicited a cytostatic effect on cancer cell proliferation in A549 and CHO-K1 cells, inhibited lactate production and arrested cells in G1 phase. Since respiration and glycolysis are tightly coupled in eukaryotic cells, a combination of suppressors of respiration with inhibitors of glycolysis were tested for cytotoxic phenotype. Indeed, treatment of U-87MG glioma cells with leucascandrolide A and P8A7 resulted in severe cell death. Further, rhodamine 123, an inhibitor of oxidative phosphorylation, hypersensitized tumor cells to treatment with 2-deoxyglucose that induced greater cell-cycle inhibition and cytotoxicity in tumor cells under hypoxic vs. aerobic conditions. Subsequent studies established that P9E11 rapidly inhibited cellular glucose consumption, which strongly suggested that this compound inhibited glucose uptake by direct action on one of the glucose transporters. Indeed, P9E11 elicited essentially identical activity profile to cytochalasin B, which is an established inhibitor of glucose transport.

TABLE 1

Crystal and structure refinement for Jcui01.

| | |
|---|---|
| Identification Code | Jcui01 |
| Empirical formula | $C_{28}H_{28}N_2O_7$ |
| Formula weight | 504.52 |
| Temperature | 100 K |
| Wavelength | 0.71073 Å |
| Crystal system | Triclinic |
| Space Group | P1(bar) |
| Unit cell dimensions | a = 9.485(3) Å    α = 105.968(4)° |
| | b = 10.685(3) Å    β = 106.660(4)° |
| | c = 12.690(3) Å    γ = 93.538(5)° |
| Volume | 1170.7(5) Å$^3$ |
| Z | 2 |
| Density (calculated) | 1.431 Mg/m$^3$ |
| Absorption coefficient | 0.104 mm$^{-1}$ |
| F(000) | 532 |
| Crystal size, color, habit | 0.16 × 0.16 × 0.16 mm, clear, fragment |
| Theta range for data collection | 2.01-28.43° |
| Index ranges | −12 ≤ h ≤ 12, −14 ≤ k ≤ 14, −16 ≤ l ≤ 16 |
| Reflections collected | 13,789 |
| Independent reflections | 5,535 ($R_{int}$ = 0.0374) |
| Reflections with I > 4σ($F_o$) | 3,878 |
| Absorption correction | SADABS based on redundant diffractions |
| Max. and min. transmission | 1.0, 0.742 |
| Refinement method | Full-matrix least squares on F$^2$ |
| Weighting scheme | w = q [σ$^2$ ($F_o^2$) + (aP)$^2$ + bP]$^{-1}$ where: P = ($F_o^2$ + 2 $F_c^2$)/3, a = 0.057, b = 0.0, q = 1 |
| Data/restraints/parameters | 5535/0/335 |
| Goodness-of-fit on F$^2$ | 0.886 |
| Final R indices [I > 2 sigma(I)] | R1 = 0.0470, wR2 = 0.0990 |
| R indices (all data) | R1 = 0.0697, wR2 = 0.1081 |
| Largest diff, peak and hole | 0.317, −0.213 eÅ$^{-3}$ |

ACC Activity Screen. The saturated cultures of hACC1 or hACC2 overexpressed *Saccharomyces Cerevisiae* were diluted to 0.05 O.D. with growth medium (YPRG), and were seeded into 96-well plates (about 150 µL per well). Initial optical densities were taken on a plate reader, before the treatment of library compounds (about 1 µL DMSO stock, about 100 µM final assay concentration). Optical density of each well was read after the treatment as t=0 data. The plates were incubated at 30° C. while shaking at 350-400 rpm. End point readings were taken when the plate average optical densities reached ~1.0 (36-40 hours for hACC1, 60-64 hours for hACC2). For each well, the change of optical density was calculated, and the percent inhibition was obtained by normalizing to the plate average of optical density change.

Compounds showing more than 15% growth inhibitions were selected as potential hits, and were assayed for their toxicities against wild type *Saccharomyces Cerevisiae*. The saturated cultures of wild type *Saccharomyces Cerevisiae* were diluted to about 0.05 O.D. with growth medium (YPRG), and were seeded into 96-well plates (about 150 µL per well). Initial optical densities were taken on a plate reader, before the treatment of the potential hits (about 1 µL DMSO stock, about 100 µM final assay concentration) as well as DMSO. Optical density of each well was read after the treatment as t=0 data. The plates were incubated at 30° C. while shaking at 350-400 rpm. End point readings were taken when the optical densities for the DMSO controls reached ~1.0 (16-18 hours). For each well, the change of optical density was calculated, and the percent inhibition was obtained by normalizing to the average optical density change of the DMSO controls.

Compounds showing low toxicities for wild type strain, and strong growth inhibitions for hACC1 or hACC2 strains were selected as hits for further studies.

Selectivity and Dose-Dependent Response. The saturated cultures of wide type, hACC1 overexpressed and hACC2 overexpressed *Saccharomyces Cerevisiae* were diluted to about 0.05 O.D. with growth medium (YPRG), and were seeded into 96-well plates (about 150 µL per well). The cultures were incubated with different concentrations of JC10F11 and DMSO vector at 30° C. while shaking at 350-400 rpm. End point readings were taken when the average optical densities for the DMSO controls reached ~1.0 (16 hours for wild type, 36 hours for ACC1 and 62 hours for ACC2). For each strain and concentration, the percent optical density against DMSO control was plotted as a bar graph using Excel.

Efficient generation and screening of new small-molecule libraries is an integral component of drug discovery, which enables the identification of previously unknown bioactive chemotypes for subsequent basic and translational biomedical research. The present disclosure provides a simple, practical and general strategy for rapid access to chemical libraries, which are produced in high chemical purity via a combination of solution-phase high-throughput organic synthesis and the parallel preparative thin layer chromatographic (TLC) purification of each library member. The method is based on miniaturization of the reaction scale of solution-phase organic synthesis, which enables efficient preparation and purification of each individual library member. The assembly process does not require any specialized equipment, and represents a highly economical and facile method for generating molecular diversity in high chemical purity. This strategy has a potential for the production of a wide range of chemical libraries for lead discovery and optimization.

While the present disclosure has been described with reference to certain embodiments, other features may be included without departing from the spirit and scope of the present invention. It is therefore intended that the foregoing detailed description be regarded as illustrative rather than limiting, and that it be understood that it is the following claims, including all equivalents, that are intended to define the spirit and scope of this invention.

The invention claimed is:

1. A compound of the formula (II):

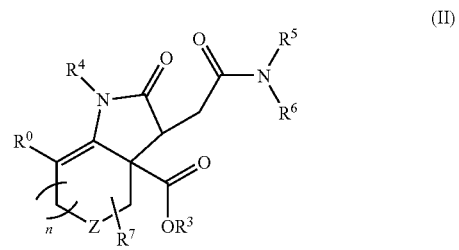

or a pharmaceutically acceptable salt thereof, where $R^0$ is hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R'", —NR'R", —NR'CO$_2$R", —NR'S(O)$_2$R", —SR', —S(O)R', —S(O)$_2$R', —S(O)$_2$NR'R", or $C_{6-10}$ aryl, where $R^3$ is hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", —NR'C(O)R", —NR'C(O)NR"R'", —NR'R", —NR'CO$_2$R", —NR'S(O)$_2$R", or $C_{6-10}$ aryl, where $R^4$, $R^5$, and $R^6$ are each independently hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", or $C_{6-10}$ aryl, and $R^5$ and $R^6$ may, together with the atoms to which they are attached, form a 3- to 10-membered ring, where Z is carbon, nitrogen, oxygen, or sulfur, where n is 0-3, where $R^7$ can substitute any open valence of any ring within the structure, and $R^7$ is hydrogen, halogen, $C_{1-20}$ alkyl, $C_{2-8}$ alkenyl, —$C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R'", —NR'R", —NR'CO$_2$R", —NR'S(O)$_2$R", —SR', —S(O)R', —S(O)$_2$R', —S(O)$_2$NR'R", $C_{6-10}$ aryl, and where R', R" and R'" are each independently selected from the group consisting of hydrogen, $C_{1-8}$ alkyl, $C_{2-8}$ alkenyl, $C_{2-8}$ alkynyl, $C_{6-10}$ aryl, 5- to 10-membered heteroaryl, and 3- to 10-membered heterocyclyl; and R' and R" or R" and R'" may, together with the atoms to which they are attached, form a 3- to 10-membered ring.

2. The compound of claim 1, where $R^0$ is hydrogen.

3. The compound of claim 1, where $R^3$ is hydrogen or $C_{1-20}$ alkyl.

4. The compound of claim 1, where $R^3$ is ethyl.

5. The compound of claim 1, where $R^5$ and $R^6$, together with the atoms to which they are attached, form a 5- to 10-membered ring which is carbocyclic, aryl, heterocyclic, or heteroaryl.

6. The compound of claim 1, where n is 2, Z is carbon, and $R^0$ and $R^7$ are hydrogen.

7. The compound of claim 1, which is of the formula (III):

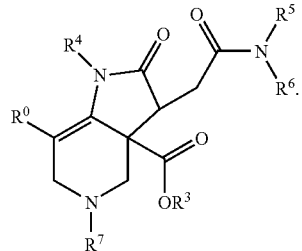
(III)

8. The compound of claim 1, which is of the formula (IV):

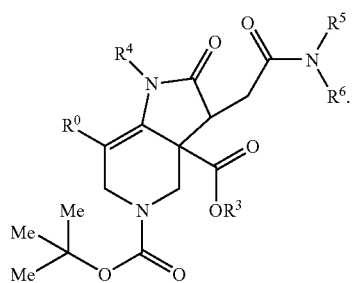
(IV)

9. The compound of claim 1, which is of the formula (Vb):

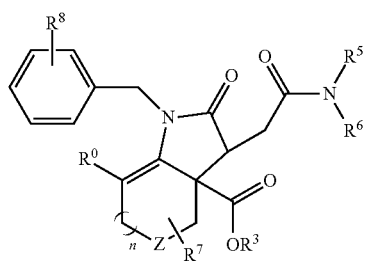
(Vb)

where $R^8$ can substitute any open valence of any ring within the structure, and $R^8$ is hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R''', —NR'R", —NR'CO$_2$R", —NR'S(O)$_2$R", —SR', —S(O)R', —S(O)$_2$R', —S(O)$_2$NR'R", $C_{6-10}$ aryl, 5- to 10-membered heteroaryl, or 3- to 10-membered heterocyclyl, or two $R^8$ groups may, together with the atoms to which they are attached, form a 3- to 10-membered ring.

10. A compound of the formula (VIa):

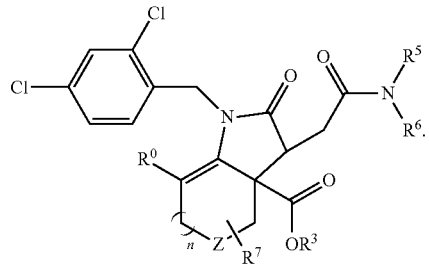
(VIa)

or a pharmaceutically acceptable salt thereof, where $R^0$ is hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R''', —NR'R", —NR'CO$_2$R", —NR'S(O)$_2$R", —SR', —S(O)R', —S(O)$_2$R', —S(O)$_2$NR'R", or $C_{6-10}$ aryl, where $R^3$ is hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", —NR'C(O)R", —NR'C(O)NR"R''', —NR'R", —NR'CO$_2$R", —NR'S(O)$_2$R", or $C_{6-10}$ aryl, where $R^5$, and $R^6$ are each independently hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", or $C_{6-10}$ aryl, and $R^5$ and $R^6$ may, together with the atoms to which they are attached, form a 3- to 10-membered ring, where Z is carbon, nitrogen, oxygen, or sulfur, where n is 0-3, where $R^7$ can substitute any open valence of any ring within the structure, and $R^7$ is hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R''', —NR'R", —NR'CO$_2$R", —NR'S(O)$_2$R", —SR', —S(O)R', —S(O)$_2$R', —S(O)$_2$NR'R", $C_{6-10}$ aryl, and where R', R" and R''' are each independently selected from the group consisting of hydrogen, $C_{1-8}$ alkyl, $C_{2-8}$ alkenyl, $C_{2-8}$ alkynyl, $C_{6-10}$ aryl, 5- to 10-membered heteroaryl, and 3- to 10-membered heterocyclyl; and R' and R" or R" and R''' may, together with the atoms to which they are attached, form a 3- to 10-membered ring.

11. The compound of claim 1, which is of the formula (VIIb):

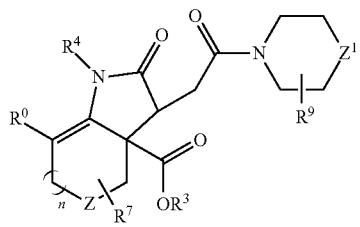
(VIIb)

where $Z^1$ is carbon, nitrogen, oxygen, or sulfur, and where $R^9$ can substitute any open valence of any ring within the structure, and $R^9$ is hydrogen, halogen, $C_{1-20}$ alkyl, $C_{2-8}$ alkenyl, $C_{2-8}$ alkynyl, —CN, —NO$_2$, —C(O)R', —CO$_2$R', —C(O)NR'R", —OR', —OC(O)R', —OC(O)NR'R", —NR'C(O)R", —NR'C(O)NR"R''', —NR'R", —NR'CO$_2$R", —NR'S(O)$_2$R", —SR', —S(O)R', —S(O)$_2$R', —S(O)$_2$NR'R", $C_{6-10}$ aryl, 5- to 10-membered heteroaryl, or 3- to 10-membered heterocyclyl, or two $R^9$ groups may, together with the atoms to which they are attached, form a 3- to 10-membered ring.

12. The compound of claim 1, which is of the formula (VIIIa):

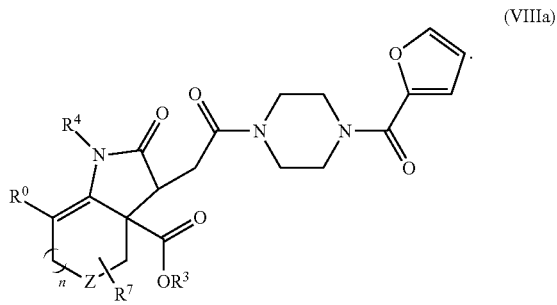

13. The compound of claim 1, which is of the formula (IX):

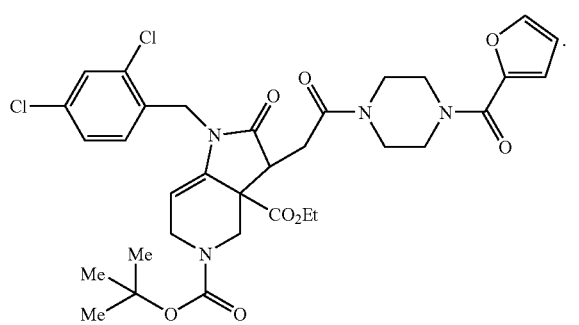

14. A compound of the formula (X):

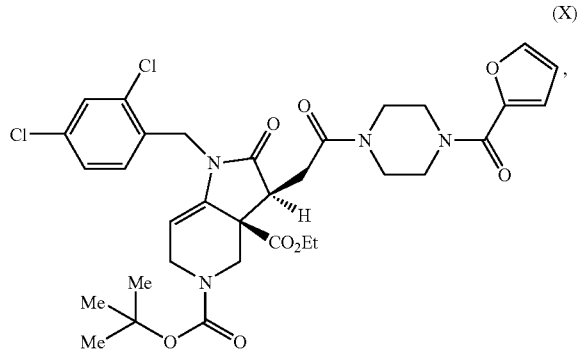 [SMILES: CCOC(=O)[C@@]12CN(C(=O)OC(C)(C)C)CC=C1N(Cc1ccc(Cl)cc1Cl)C(=O)[C@H]2CC(=O)N1CCN(C(=O)c2ccco2)CC1]

or a pharmaceutically acceptable salt thereof.

15. A composition, comprising:

the compound of claim 1 or 14, or a pharmaceutically acceptable salt thereof.

16. A pharmaceutical composition, comprising:

the compound of claim 1 or 14, or a pharmaceutically acceptable salt thereof; and a pharmaceutical acceptable carrier.

17. The compound of claim 1, which is

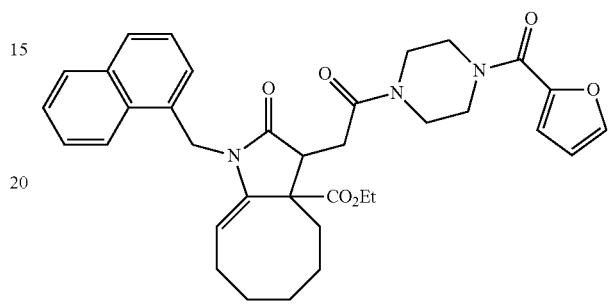

or a pharmaceutically acceptable salt thereof.

18. The compound of claim 1, which is

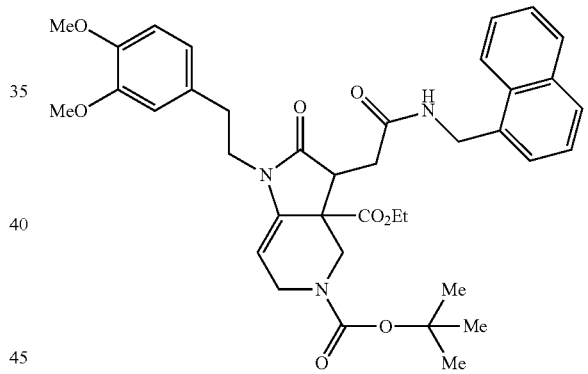

or a pharmaceutically acceptable salt thereof.

* * * * *